United States Patent [19]

MacLeay

[11] Patent Number: 5,043,372

[45] Date of Patent: Aug. 27, 1991

[54] N,N'-HYDROCARBYLENEBIS[N-HALS-SUBSTITUTED AMIC ACID HYDRAZIDES] AND THEIR DERIVATIVES

[75] Inventor: Ronald E. MacLeay, Amherst, N.Y.

[73] Assignee: Atochem North America, Inc., Philadelphia, Pa.

[21] Appl. No.: 454,889

[22] Filed: Dec. 22, 1989

[51] Int. Cl.$^5$ .................. C08K 5/3435; C07D 211/30
[52] U.S. Cl. ...................................... 524/103; 524/89; 524/94; 546/187; 546/190
[58] Field of Search ...................... 524/103, 89, 99; 546/187, 190

[56] References Cited

U.S. PATENT DOCUMENTS

| | | | |
|---|---|---|---|
| 4,145,512 | 3/1979 | Uhrhan et al. | 528/73 |
| 4,153,596 | 5/1979 | Oertel et al. | 106/125 |
| 4,178,279 | 12/1979 | Uhrhan et al. | 8/178 E |
| 4,191,683 | 3/1980 | Brunetti et al. | 106/124 |
| 4,223,147 | 9/1980 | Oertel et al. | 546/224 |
| 4,336,183 | 6/1982 | Nakahara et al. | 524/95 |
| 4,348,524 | 9/1982 | Karrer et al. | 546/187 |
| 4,857,595 | 8/1989 | Kazmierczak et al. | 525/142 |
| 4,857,596 | 8/1989 | MacLeay et al. | 525/142 |

FOREIGN PATENT DOCUMENTS

| | | |
|---|---|---|
| 1190038 | 7/1985 | Canada . |
| 22997 | 1/1981 | European Pat. Off. . |
| 219333 | 4/1987 | European Pat. Off. . |
| 79-95649 | 7/1979 | Japan . |
| 79-103461 | 8/1979 | Japan . |
| 2174093 | 10/1986 | United Kingdom . |

OTHER PUBLICATIONS

Encyclopedia of Polymer Science and Engineering, 2nd Ed., vol. 2, pp. 83–84, *Chemical Abstracts*, 97:217369g (1982).

*Primary Examiner*—Kriellion S. Morgan
*Attorney, Agent, or Firm*—Panitch Schwarze Jacobs & Nadel

[57]  ABSTRACT

N,N'-hydrocarbylenebis[N-(2,2,6,6-tetraalkyl-4-piperidinyl)amic acid hydrazides] and their derivatives are useful for stabilizing polymeric systems which are subject to degradation and/or discoloration upon exposure to heat and/or light. The novel compounds contain at least two hindered amine light stabilizing groups and two hydrazide or hydrazide derivative thermal oxidative stabilizing groups.

The novel compounds are excellent light stabilizers for polyolefins, have low volatility and are not readily lost from polymeric systems via volatilization, migration or extraction.

30 Claims, No Drawings

N,N'-HYDROCARBYLENEBIS[N-HALS-SUBSTITUTED AMIC ACID HYDRAZIDES] AND THEIR DERIVATIVES

BACKGROUND OF THE INVENTION

1. Field of the Invention

This invention relates to N,N'-hydrocarbylenebis[N-(2,2,6,6-tetraalkyl-4-piperidinyl)amic acid hydrazides] and their derivatives. These compounds are useful for stabilizing polymeric systems which are subject to degradation and/or discoloration upon exposure to heat and/or light. These compounds contain at least two hindered amine light stabilizing groups (HALS groups) and two hydrazide (or hydrazide derivative) thermal oxidative stabilizing groups.

The amic acid hydrazide functionality in these compounds enhances the photooxidative stabilizing properties of the hindered amine groups and contributes thermooxidative stabilizing and metal complexing properties to the compounds.

The non-derivatized bis hydrazide precursors are reactive stabilizers that can be attached to compounds containing anhydride or carboxylic acid groups. Due to the reactive bis hydrazide groups they can be incorporated into polyesters, polyamides, polyimides or combinations thereof, during the polymerization step to form permanently bound stabilizing groups.

The novel derivatives of the hydrazides have low volatility and are not readily lost from polymeric systems via volatilization, migration or extraction.

2. Description of the Prior Art

It is well known in the art to use hindered amine compounds to retard the deleterious effect of ultraviolet radiation on synthetic polymers. Hydrazides and hydrazide derivatives are used commercially for stabilizing polyolefins. (See *Encyclopedia of Polymer Science and Engineering*, 2nd Ed. Vol. 2, pp. 83–84 (1985)). However, there are only four examples in the literature where the hindered amine moiety and the hydrazide moiety (—R—C(=O)—NH—NH$_2$, where R is not O, N or S) are present in the same molecule. None of these examples have more than one hindered amine moiety in the molecule. None of these prior art compounds are hydrazides of amic acids.

Previously known HALS hydrazides are:

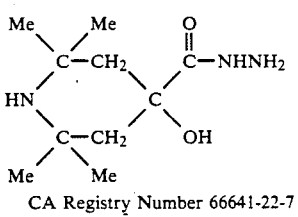

CA Registry Number 66641-22-7
U.S. Pat. No. 4,153,596 and 4,223,147

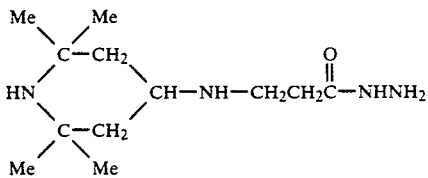

CA Registry Number 66651-23-8
U.S. Pat. No. 4,153,596 and 4,223,147

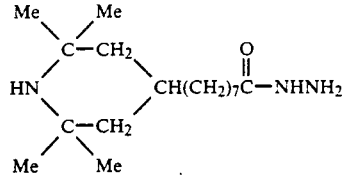

CA Registry Number 72436-11-4
JP 79/103461; CA92:59703j
JP 79/95649; CA92:42845j

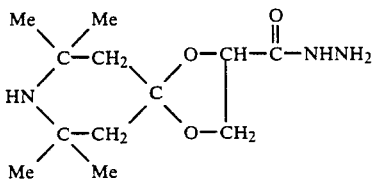

CA Registry Number 77246-76-5
U.S. Pat. No. 4,336,183; CA97:217369g
E.P. Appl. 22997; CA94:176176s U S. Pat. Nos. 4,145,512 and 4,178,279 teach reacting hindered amine light stabilizers containing carboxylic acid hydrazide groups with isocyanate groups of polyisocyanates or isocyanate prepolymers to obtain light stabilized polyurethanes. However, the HALS-hydrazides employed were of the prior-art type. They did not have the amic acid hydrazide structure which enhances the light stabilizing properties of our novel compounds.

Although they are not "prior art," copending U.S. Pat. application Ser. No. 310,408, filed Feb. 13, 1989, and abandoned parent U.S. Pat. application Ser. No. 84,602, filed Aug. 12, 1987, both assigned to the assignee of the present invention and application, disclose N-(2,2,6,6-tetraalkyl-4-piperidinyl)amic acid hydrazides having the general formula:

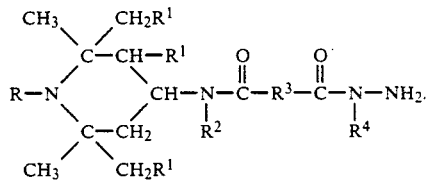

These amic acid hydrazides are efficient light stabilizers, the hydrazide group providing a means of attaching the light stabilizer to anhydride containing copolymers.

U.S. Pat. No. 4,857,595, assigned to the assignee of the present invention and application, discloses HALS hydrazides attached to maleic anhydride copolymers.

U.S. Pat. No. 4,857,596, also assigned to the assignee of the present invention and application, discloses polyfunctional polymers or copolymers in which HALS hydrazides and UV absorbers or antioxidants are attached to anhydride containing polymers or copolymers.

All of the prior art hydrazides substituted with hindered amine light stabilizing groups are of relatively low molecular weight. Appreciable amounts of these stabilizers may be lost due to volatilization during processing when incorporated into polyolefins or engineering thermoplastics. None of the prior art hydrazides fall under general structure I of the present invention. None of the prior art hydrazides contain more than one reactive hydrazide group in the structure.

In addition, the prior art HALS hydrazides may only be attached to polyurethanes, polyesters, polycarbonates, polyamides or polyimides as end-capping groups. The prior art HALS hydrazides cannot be incorporated into the backbone of the polymers.

DEFINITIONS

Throughout the disclosure, when referring to "2,2,6,6-tetraalkylpiperidines" or "2,2,6,6-tetraalkyl-4-piperidinyl groups", the piperidinyl groups optionally substituted in the 3 position of the piperidine group with lower alkyl groups of 1–4 carbons are also included, i.e., the structure having the formula:

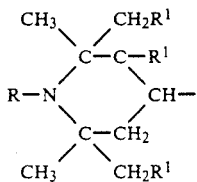

where R and $R^1$ are as defined hereinafter.

The term "acyl" refers to a radical generated from a carboxylic acid by the removal of the OH group to provide a free valence on the C(=O) group, for example, DC(=O)OH would become the DC(=O) substituent referred to generally as a D acyl group.

The terms "polymer" or "polymeric composition(s)" include homopolymers or any type of copolymers.

Where any symbol appears more than once in a formula, its meaning in each instance is independent of one another.

SUMMARY OF THE INVENTION

This invention comprises an N,N'-hydrocarbylenebis[N-(2,2,6,6-tetraalkyl-4-piperidinyl)amic acid hydrazide] and its derivatives having the following Formula I:

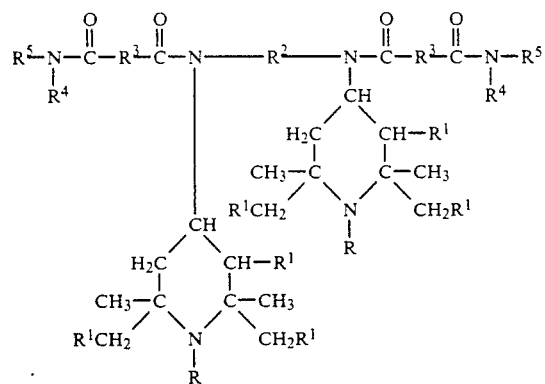

wherein

R is hydrogen; oxyl; hydroxy; substituted or unsubstituted aliphatic of 1 to 20 carbons; substituted or unsubstituted araliphatic of 7 to 22 carbons; substituted or unsubstituted aliphatic acyl of 2 to 20 carbons; substituted or unsubstituted alicyclic acyl of 6–13 carbons; substituted or unsubstituted aromatic acyl of 7 to 20 carbons, substituted or unsubstituted araliphatic acyl of 8 to 16 carbons; where the substituents for all of the above substituted groups are at least one of chlorine, bromine, alkyl of 1 to 8 carbons, alkoxy of 1 to 8 carbons, phenoxy, cyano, hydroxy or epoxy; alkoxycarbonyl of 2 to 9 carbons; cycloalkoxycarbonyl of 6 to 13 carbons; aryloxycarbonyl of 7 to 15 carbons; mono-substituted carbamoyl, where the substituent is alkyl of 1 to 20 carbons, cycloalkyl of 5 to 12 carbons, aralkyl of 7 to 15 carbons or aryl of 6 to 14 carbons; di-substituted carbamoyl, where the substituents are independently alkyl of 1 to 20 carbons, cycloalkyl of 5 to 12 carbons or aralkyl of 7 to 15 carbons; 2-cyanoethyl; hydroxyalkyl of 2 to 6 carbons; epoxyalkyl of 3 to 10 carbons or polyalkylene oxide of 4 to 30 carbons;

$R^1$ is hydrogen or lower alkyl of 1 to 4 carbons;

$R^2$ is an alkylene diradical of 2 to 18 carbons, an alkylene diradical of 4 to 18 carbons containing 1 to 2 —O—, —S— or —NH— heteroatoms, with the proviso that multiple heteroatoms must be separated from each other and the diradical ends by at least one carbon atom, a cycloalkylene diradical of 5 to 18 carbons, an alkylidenedicycloalkylene diradical of 14 to 18 carbons, a cycloalkylenedialkylene diradical of 14 to 18 carbons, an alkylene-dicycloalkylene diradical of 14 to 18 carbons, an arylene diradical of 6 to 12 carbons, an alkylenediarylene diradical of 13 to 18 carbons, an alkylidenediarylene diradical of 14 to 18 carbons or an aralkylene diradical of 8 to 18 carbons;

$R^3$ is a direct bond, an alkylene diradical of 1 to 14 carbons, an alkenylene diradical of 2 to 10 carbons, an oxydialkylene diradical of 4 to 10 carbons, a thiodialkylene diradical of 4 to 10 carbons or a substituted or unsubstituted o-, m- or p-phenylene diradical, where the substituents are lower alkyl of 1 to 6 carbons, hydroxy, bromine, chlorine, mercapto or lower alkylmercapto of 1 to 6 carbons;

$R^4$ is hydrogen, alkyl of 1 to 8 carbons, aralkyl of 7 to 12 carbons or cycloalkyl of 5 to 12 carbons;

$R^5$ is $(R^6)(R^7)N—$, $(R^8)(R^9)C=N—$, MOC(-=O)—$R^{10}$—C(=O)—N($R^6$)— or

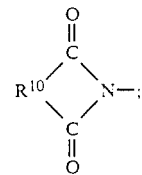

$R^6$ is hydrogen, alkyl of 1 to 12 carbons, cycloalkyl of 5 to 12 carbons, aralkyl of 7 to 12 carbons or aryl of 6 to 14 carbons;

$R^7$ is hydrogen; lower alkyl of 1 to 4 carbons; substituted or unsubstituted aliphatic acyl of 2 to 20 carbons, substituted or unsubstituted alicyclic acyl of 6 to 13 carbons, substituted or unsubstituted araliphatic acyl of 8 to 16 carbons, substituted or unsubstituted aromatic acyl of 7 to 20 carbons, where the substituents for the substituted acyl groups are at least one of chlorine, bromine, alkyl of 1 to 8 carbons, alkoxy of 1 to 8 carbons, phenoxy, cyano, hydroxy or epoxy; alkoxycarbonyl of 2 to 13 carbons; cycloalkoxycarbonyl of 6 to 13 carbons; aryloxycarbonyl of 7 to 15 carbons; hydroxyalkyl of 2 to 6 carbons; carbamoyl; thiocarbamoyl; mono-substituted carbamoyl or mono-substituted thiocarbamoyl, where the substituent is alkyl of 1 to 20 carbons, alkenyl of 3 to 12 carbons, cycloalkyl of 5 to 12 carbons, substituted or unsubstituted aralkyl of 7 to 15 carbons or substituted or unsubstituted aryl of 6 to 14 carbons; or di-substituted carbamoyl or di-substituted thiocarbamoyl, where the substituents are independently alkyl of 1 to 20 carbons, cycloalkyl of 5 to 12 carbons, substituted or unsubstituted aralkyl of 7 to 15 carbons or substituted or unsubstituted aryl of 6 to 14 carbons, where the substituents for the substituted aralkyl group and the substituted aryl group for both the mono- and di-substituted carbamoyl groups are at least one of chlorine, bromine, alkyl of 1 to 8 carbons, alkenyl of 3 to 8 carbons or alkoxy of 1 to 8 carbons;

$R^8$ and $R^9$ are independently hydrogen, alkyl of 1 to 12 carbons, cycloalkyl of 5 to 12 carbons or substituted or unsubstituted aryl of 6 to 18 carbons, where the substituents are lower alkyl of 1 to 8 carbons, lower alkoxy of 1 to 8 carbons, hydroxy, bromine or chlorine; or $R^8$ and $R^9$ are linked together to form a substituted or unsubstituted alicyclic ring of 5 to 12 carbons, where the substituents are lower alkyl of 1 to 4 carbons; or $R^8$ and $R^9$ together form a substituted or unsubstituted piperidine ring of 5 to 15 carbons, where the substituents are lower alkyl of 1 to 4 carbons;

$R^{10}$ is a substituted or unsubstituted 1,2-arylene diradical of 6 to 12 carbons, a substituted or unsubstituted 1,8-naphthylene diradical of 10 to 14 carbons, a substituted or unsubstituted aralkylene diradical of 7 to 13 carbons, a substituted or unsubstituted 1,2-alkylene diradical of 2 to 10 carbons, a substituted or unsubstituted 1,3-alkylene diradical of 3 to 10 carbons, a substituted or unsubstituted alkene-1,2-diyl of 2 to 10 carbons, a substituted or unsubstituted, saturated or unsaturated cycloalkylene diradical of 6 to 10 carbons or a substituted or unsubstituted, saturated or unsaturated bicycloalkylene diradical of 7 to 8 carbons, where the $R^{10}$ substituents are chlorine, bromine, alkyl of 1 to 180 carbons, alkylthio of 1 to 180 carbons, aralkylthio of 7 to 20 carbons, arylthio of 6 to 20 carbons, alkenyl of 2 to 180 carbons, aryl of 6 to 16 carbons, aralkyl of 7 to 17 carbons, carboxyl, alkoxy of 1 to 8 carbons, aryloxy of 6 to 16 carbons, alkoxycarbonyl of 2 to 10 carbons or alkoxycarbonylalkylthio of 3 to 30 carbons; and M is hydrogen or a sodium, potassium or ammonium ion.

Preferably, R is hydrogen, alkyl of 1 to 4 carbons, alkenyl of 3 to 4 carbons, benzyl, 2-cyanoethyl, acetyl or benzoyl.

More preferably, R is hydrogen, methyl, acetyl or benzoyl.

Preferably, $R^1$ is hydrogen or methyl and is more preferably hydrogen.

Preferably, $R^2$ is an alkylene diradical of 2 to 12 carbons, an alkylene diradical of 4 to 12 carbons which contains 1 to 2 —O— or —NH— heteroatoms with the proviso that multiple heteroatoms must be separated from each other and the diradical ends by at least one carbon atom, a cycloalkylene diradical of 5 to 12 carbons, an arylene diradical of 6 to 12 carbons or an aralkylene diradical of 8 to 12 carbons.

More preferably, $R^2$ is an alkylene diradical of 2 to 6 carbons or an oxydialkylene diradical of 4 to 8 carbons.

Preferably, $R^3$ is a direct bond, an alkylene diradical of 1 to 8 carbons or an o-, m-or p-phenylene diradical.

More preferably, $R^3$ is a direct bond or an alkylene diradical of 1 to 7 carbons.

Preferably, $R^4$ is hydrogen, primary alkyl of 1 to 4 carbons, secondary alkyl of 3 to 8 carbons, benzyl or cyclohexyl.

More preferably, $R^4$ is hydrogen or methyl.

Preferably, $R^6$ is hydrogen, lower alkyl of 1 to 4 carbons, cyclohexyl, benzyl or phenyl.

More preferably, $R^6$ is hydrogen.

Preferably, $R^7$ is hydrogen; methyl; ethyl; cylcohexyl; aliphatic acyl of 2 to 10 carbons; substituted or unsubstituted araliphatic acyl of 7 to 22 carbons; substituted or unsubstituted aromatic acyl of 7 to 15 carbons, where the substituents are at least one of alkyl of 1 to 5 carbons, alkoxy of 1 to 5 carbons or hydroxy; alkoxycarbonyl of 2 to 9 carbons; aryloxycarbonyl of 7 to 10 carbons; alkylcarbamoyl of 2 to 19 carbons; cycloalkylcarbamoyl of 6 to 13 carbons; aryl carbamoyl of 7 to 10 carbons or aralkylcarbamoyl of 8 to 14 carbons.

More preferably, $R^7$ is hydrogen, methyl, methylcarbamoyl, butylcarbamoyl, octadecylcarbamoyl, phenylcarbamoyl, acetyl, propionyl, benzoyl, 3,5-di-t-butyl-4-hydroxybenzoyl, methoxycarbonyl, ethoxycarbonyl or 2-ethylhexoxycarbonyl.

Preferably, $R^8$ and $R^9$ are independently hydrogen, alkyl of 1 to 8 carbons, cycloalkyl of 5 to 6 carbons, substituted or unsubstituted aryl of 6 to 14 carbons, where the substituents are hydroxy and lower alkyl of 1 to 4 carbons; or $R^8$ and $R^9$ are linked together to form an alicyclic ring of 5 to 8 carbons; or $R^8$ and $R^9$ together form a tetraalkyl-substituted piperidine ring, where the substituents are methyl or ethyl in the 2 and 6 positions of the piperidine ring.

More preferably, $R^8$ and $R^9$ are independently lower alkyl of 1 to 4 carbons or are linked together to form a 5 or 6-membered aliphatic ring or $R^8$ and $R^9$ together form a 2,2,6,6-tetramethyl-4-piperidinyl ring.

Preferably, $R^{10}$ is substituted or unsubstituted 1,2-ethenediyl, substituted or unsubstituted 1,2-ethanediyl, substituted or unsubstituted 1,2-propanediyl, substituted or unsubstituted 1,3- propanediyl, substituted or unsubstituted 1,2-cyclohexanediyl, substituted or unsubstituted cyclohex-4-ene-1,2-diyl, substituted or unsubstituted norborn-5-ene-2,3-diyl, substituted or unsubstituted 2,3-norbornanediyl, substituted or unsubstituted bicyclo[2.2.2]oct-5-ene-2,3-diyl or a substituted or unsubstituted o-phenylene diradical, where the substituents are chlorine, bromine, alkyl of 1 to 36 carbons, alkenyl of 2 to 36 carbons, aryl of 6 to 10 carbons, aralkyl of 7 to 13 carbons, alkylthio of 1 to 36 carbons, aralkylthio of 7 to 14 carbons, arylthio of 6 to 12 carbons, carboxyl, alkoxy of 1 to 8 carbons, aryloxy of 6 to 12 carbons or alkoxycarbonyl of 2 to 5 carbons.

More preferably, $R^{10}$ is 1,2-ethanediyl substituted by alkyl of 1 to 18 carbons or alkenyl of 2 to 18 carbons; 1,2-cyclohexanediyl; 4-methylcyclohexane-1,2-diyl; cyclohex-4-ene-1,2-diyl; 2,3-norbornanediyl; norborn-5-ene-2,3-diyl; an o-phenylene diradical or a 4-methoxycarbonyl-o-phenylene diradical.

Preferably, M is hydrogen or a sodium ion and more preferably, M is hydrogen.

This invention also comprehends stabilizing polymeric systems against the degradative effects of heat and/or light by including an effective amount of a Formula I compound in the polymeric system.

This invention also comprehends processes for preparing the Formula I compound.

DETAILED DESCRIPTION OF THE PREFERRED EMBODIMENTS

The Formula I compounds of this invention are novel polymer additives containing light stabilizing groups and thermal stabilizing groups in the same molecule.

The invention also provides novel polymer additives which incorporate two hindered amine light stabilizing groups and two hydrazide heat stabilizer groups in the same molecule.

This invention further provides stabilized polymeric compositions containing these novel additives.

Illustrative, non-limiting examples of the various constituent R groups defined hereinbefore are as follows:

For R: hydrogen, oxygen, methyl, ethyl, propyl, butyl, hexyl, heptyl, octyl, nonyl, decyl, dodecyl, tetradecyl, octadecyl, allyl, 2-methallyl, 2-butenyl, 2-hexenyl, 10-undecenyl, 2-dodecenyl, propargyl, benzyl, methylbenzyl, 4-t-butylbenzyl, 3,5-di-t-butyl-4-hydroxybenzyl, formyl, acetyl, propionyl, butyryl, caproyl, capryloyl, lauroyl, acryloyl, methacryloyl, crotonyl, benzoyl, o-methylbenzoyl, 3,5-di-t-butyl-4-hydroxybenzoyl, methoxycarbonyl, ethoxycarbonyl, 2-ethylhexoxycarbonyl, cyclopentoxycarbonyl, cyclohexoxycarbonyl, cyclododecoxycarbonyl, phenoxycarbonyl, o-methylphenoxycarbonyl, isopropoxycarbonyl, N,N-dimethylcarbamoyl, N-butylcarbamoyl, N-methylcarbamoyl, N-octadecylcarbamoyl, N-cyclohexylcarbamoyl, N-phenylcarbamoyl, N-benzylcarbamoyl, 2-cyanoethyl, 2-hydroxyethyl, 2-hydroxypropyl, 2,3-epoxypropyl, poly(ethyleneoxy) or poly(propyleneoxy).

For $R^1$: hydrogen, methyl, ethyl, propyl, butyl.

For $R^2$: 1,2-ethanediyl, 1,2-propanediyl, 1,3=propanediyl, 1,4-butanediyl, 1,5-pentanediyl, 1,6-hexanediyl, 1,18-octadecanediyl, 2,2-dimethylpropane-1,3-diyl, 2-methylpentane-2,4-diyl, 1,10-decanediyl, 1,12-dodecanediyl, 3-oxapentane-1,5-diyl, 4-oxaheptane-1,7-diyl, 3,6-dioxaoctane-1,8-diyl, 4,9-dioxadodecane-1,12-diyl, 4-methyl-azaheptane-1,4-diyl, 3,6-diaza-3,6-dimethyl-1,8-octanediyl, 3-methyl-3-azapentane-1,5-diyl, 1,2-cyclohexanediyl, 1,4-cyclohexanediyl.

For $R^3$: a direct bond, methylene, 1,2-ethanediyl, 1,2-propanediyl, 1,3-propanediyl, 1,4-butanediyl, 1,5-pentanediyl, 1,6-hexanediyl, 1,7-heptanediyl, 1,8-octanediyl, 1,10-decanediyl, 1,12-dodecanediyl, 1,14-tetradecanediyl, an ethenylene diradical, 2-buten-1,4-diyl, 3-hexen-1,6-diyl, 5-decen-1,10-diyl, 4-oxa-1,7-heptanediyl, 5-oxa-1,9-nonanediyl, 3-thia-1,5-pentanediyl, an o-, m- or p-phenylene diradical, 4-methyl-o-phenylene, 4-chloro-o-phenylene or 4-methylmercapto-o-phenylene.

For $R^4$: hydrogen, methyl, ethyl, propyl, isopropyl, butyl, sec-butyl, isobutyl, pentyl, octyl, 2-ethylhexyl, benzyl, alpha-methylbenzyl, 4-sec-butyl-alpha-methylbenzyl, cyclopentyl, cyclohexyl, cyclooctyl or cyclododecyl.

For $R^6$: hydrogen, methyl, ethyl, propyl, isopropyl, butyl, sec-butyl, t-butyl, t-octyl, dodecyl, cyclopentyl, cyclohexyl, cycloheptyl, cyclododecyl, benzyl, alpha-methylbenzyl, 4-t-butyl-alpha-methylbenzyl, alpha,alpha-dimethylbenzyl, phenyl, naphthyl, biphenyl or phenanthryl.

For $R^7$: hydrogen, methyl, ethyl, propyl, isopropyl, butyl, sec-butyl, isobutyl, t-butyl, acetyl, propionyl, butyryl, caproyl, pivaloyl, capryloyl, lauroyl, eicosanoyl, cyclopentanecarbonyl, cyclohexanecarbonyl, cyclododecanecarbonyl, benzoyl, o-methylbenzoyl, 3,5-di-t-butyl-4-hydroxybenzoyl, 3-(3,5-di-t-butyl-4-hydroxyphenyl)propionyl, acryloyl, methacryloyl, methoxycarbonyl, ethoxycarbonyl, isopropoxycarbonyl, 2-ethylhexoxycarbonyl, dodecoxycarbonyl, cyclopentoxycarbonyl, cyclohexoxycarbonyl, cyclododecoxycarbonyl, phenoxycarbonyl, 2-hydroxyethyl, 2-hydroxy-2-methylethyl, 2-hydroxyhexyl, carbamoyl, methylcarbamoyl, N,N-dimethylcarbamoyl, N,N-diethylcarbamoyl, butylcarbamoyl, octylcarbamoyl, allylcarbamoyl, octadecylcarbamoyl, cyclohexylcarbamoyl, cyclododecylcarbamoyl, phenylcarbamoyl, biphenylcarbamoyl, naphthylcarbamoyl, benzylcarbamoyl, alpha,alpha-dimethylbenzylcarbamoyl, alpha,alpha-dimethyl-m-isopropenylbenzylcarbamoyl, alpha,alpha-dimethyl-p-isopropylbenzylcarbamoyl, methylthiocarbamoyl, butylthiocarbamoyl, octadecylthiocarbamoyl, cyclohexylthiocarbamoyl, alpha,alpha-dimethylbenzyl thiocarbamoyl, phenylthiocarbamoyl, naphthylthiocarbamoyl or phenanthrylthiocarbonyl.

For $R^8$ and $R^9$, independently: hydrogen, methyl, ethyl, propyl, isopropyl, butyl, sec-butyl, t-butyl, pentyl, hexyl, heptyl, octyl, 2-ethylhexyl, decyl, dodecyl, cyclopentyl, cyclohexyl, cyclododecyl, phenyl, m-methoxyphenyl, p-chlorophenyl, o-bromophenyl, p-hydroxyphenyl or 3,5-di-t-butyl-4-hydroxyphenyl, and when $R^8$ and $R^9$ are linked together, they may form a cyclopentyl, a cyclohexyl, a cycloheptyl, a cyclooctyl, a cyclododecyl, a piperidinyl or a 2,2,6,6-tetramethyl-4-piperidinyl ring.

For $R^{10}$: 1,2-ethenediyl, 1-chloro-1,2-ethenediyl, 1-phenyl-1,2-ethenediyl, 1,2-ethanediyl, 1,2-propanediyl, 1,3-propanediyl, 1,2-cyclohexanediyl, 4-cyclohexene-1,2-diyl, 4-methylcyclohexane-1,2-diyl, 2,3-norbornanediyl, 2,3-norborn-5-ene-2,3-diyl, bicyclo[2.2.2]oct-5-ene-2,3-diyl, an o-phenylene diradical, 4-carboxy-o-phenylene, 4-methoxycarbonyl-o-phenylene; 1-substituted 1,2-ethanediyl groups, where the substituents are alkyl or alkenyl, such as methyl, ethyl, butyl, hexyl, octyl, decyl, dodecyl, hexadecyl, octadecyl, hexenyl, isohexenyl, diisobutenyl, decenyl, dodecenyl, isododecenyl, octenyl, nonenyl, tetradecenyl, hexadecenyl, octadecenyl, isooctadecenyl, triacontenyl or polyisobutenyl; 1-substituted 1,2-ethanediyl groups, 5-substituted 2,3-norbornanediyl groups, 5-substituted bicyclo[2.2.2]-octane-2,3-diyl groups or 4-substituted-1,2-cyclohexanediyl groups, where the substituents are alkylthio, aralkylthio or arylthio, such as methylthio, ethylthio, butylthio, hexylthio, octylthio, hexadecylthio, octadecylthio, 2-hydroxyethylthio, phenylthio, benzylthio, 3,5-di-t-butyl-4-hydroxyphenylthio or 3-t-butyl-5-methyl-4-hydroxybenzylthio.

Preparation of Compounds of the Present Invention
General Preparative Methods

The novel N,N'-hydrocarbylenebis[N-(2,2,6,6-tetraalkyl-4-piperidinyl)amic acid hydrazides], designated as Formula III, corresponding to Formula I where $R^5$ is $H_2N-$ and $R^4$ is hydrogen, are prepared by the hydrazinolysis of the lower alkyl diesters of the corresponding N,N'-hydrocarbylenebis[N-(2,2,6,6-tetralkyl-4-piperidinyl)amic acids] (hereinafter "bis(half ester-half amides)")(Formula II) with hydrazine or hydrazine hydrate.

The Formula II intermediate bis(half ester-half amides) are known and their method of preparation is described in U.S. Pat. No. 4,780,493 equivalent of U.K. Patent Application GB 2,174,093A, and U.S. Pat No. 4,348,524, the disclosures of which are incorporated herein.

The unsubstituted hindered amine functions of the bis(half ester-half amides) (Formula II where R is H) can be derivatized by reacting the unsubstituted amine with alkyl halides, dimethyl sulfate, aliphatic, cycloaliphatic and aromatic acid chlorides, aliphatic, cycloaliphatic and aromatic chloroformates, dialkyl carbamoyl chlorides, aliphatic, cycloaliphatic and aromatic isocyanates, acrylonitrile, aliphatic epoxides, epichlorohydrins and alkylene oxides. These techniques are disclosed in U.S. Pat. Nos. 4,348,524 and 4,191,683 and European Patent Application Publication No. 219,333, published Apr. 22, 1987. Oxyl substituents can be introduced on the hindered nitrogen atoms by reacting the unsubstituted amine with peracids or hydrogen peroxide in the presence of tungsten catalysts (see U.S. Pat. No. 4,348,524). The oxyl radical may be converted to a hydroxyl radical in the presence of a hydrogen radical donor.

The general preparative method is illustrated by the following equation:

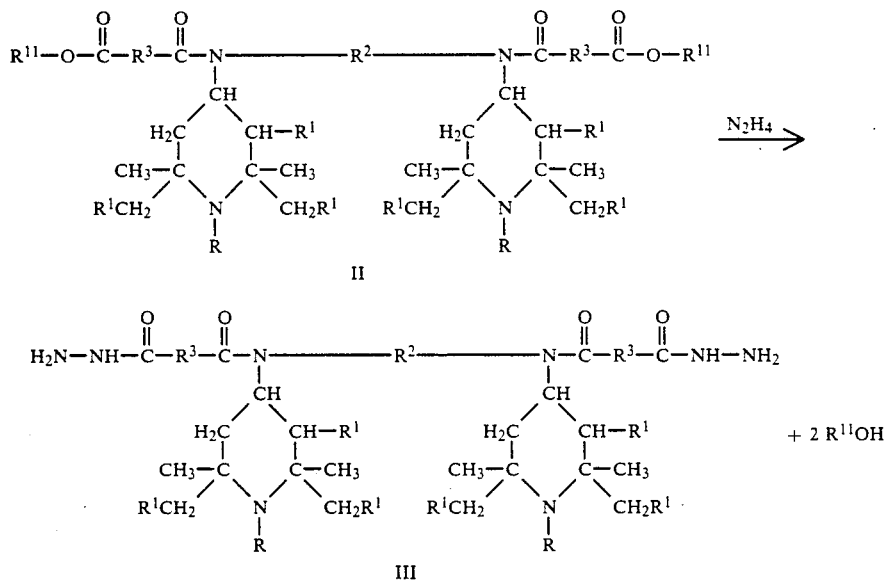

$R$, $R^1$, $R^2$ and $R^3$ are as broadly previously defined, $R^4$ is hydrogen and $R^{11}$ is lower alkyl of 1 to 4 carbons.

Preferably, the reaction is carried out with hydrazine or hydrazine hydrate in methanol or ethanol. The reaction generally proceeds at room temperature with the oxamate esters and generally requires heating or refluxing with the other amic acid esters.

Preparation of Derivatives of N,N'-Hydrocarbylenebis-[N-(2,2,6,6-tetraalkyl-4-piperidinyl)amic acid hydrazides]

I. Preparation of Hydrazone Derivatives

Method A

The novel hydrazone derivatives of Formula I, where $R^5$ is $(R^8)(R^9)C=N-$ and $R^4$ is hydrogen, designated as Formula IV, may be prepared by reacting a Formula III bis HALS amic acid hydrazide with ketones, aldehydes or formaldehyde in inert solvents, preferably in hydrocarbon solvents under azeotropic conditions. The reaction sequence of Method A is illustrated by the following equation:

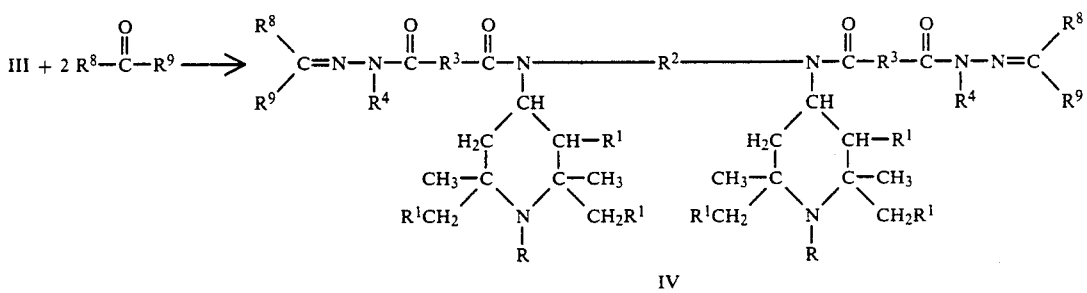

$R$, $R^1$, $R^2$, $R^3$, $R^8$ and $R^9$ are as broadly previously defined and R4 is hydrogen.

Non-limiting examples of suitable ketones include acetone, methyl ethyl ketone, 2-pentanone, 2-hexanone, 3-hexanone, 2-decanone, 3-methyl-2-pentanone, 4-methyl-2-pentanone, 4-methoxy-4-methyl-2-pentanone, cyclopentanone, cyclohexanone, cyclooctanone, cyclododecanone, 2,6-dimethyl-4-heptanone, 3,5-dimethyl-4-heptanone, 2,4-dimethyl-3-pentanone, 1,3-diphenylacetone, 2-octanone, 3-octanone, dihydroisophorone, 4-t-butylcyclohexanone, methyl cyclohexyl ketone, acetophenone, 4-piperidone, 2,2,6,6-tetramethyl-4-piperidone and 2,6-diethyl-2,6-dimethyl-4-piperidone.

Non-limiting examples of suitable aldehydes include formaldehyde, acetaldehyde, butyraldehyde, dodecyl aldehyde, 2-ethylbutyraldehyde, heptaldehyde, isobutyraldehyde, isovaleraldehyde, octyl aldehyde, propionaldehyde, valeraldehyde, benzaldehyde, 3,5-di-t-butyl-4-hydroxybenzaldehyde, 2,3-dimethyl-p-anisaldehyde, 3-hydroxybenzaldehyde, 1-naphthaldehyde, salicyaldehyde, p-tolualdehyde and 2,3,4-trimethoxybenzaldehyde.

Method B

The novel hydrazone derivatives of Formula I, where $R^5$ is $(R^8)(R^9)C=N-$ and $R$, $R^1$, $R^2$, $R^3$, $R^4$, $R^8$ and $R^9$ are as broadly previously defined (i.e., $R^4$ need not be hydrogen), designated as Formula IV, may be prepared by reacting ketone hydrazones or aldehyde hydrazones, designated each as Formula V, where $R^4$, $R^8$ and $R^9$ are as broadly previously defined, with the Formula II bis(half ester-half amides), as indicated by the following reaction equation:

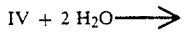

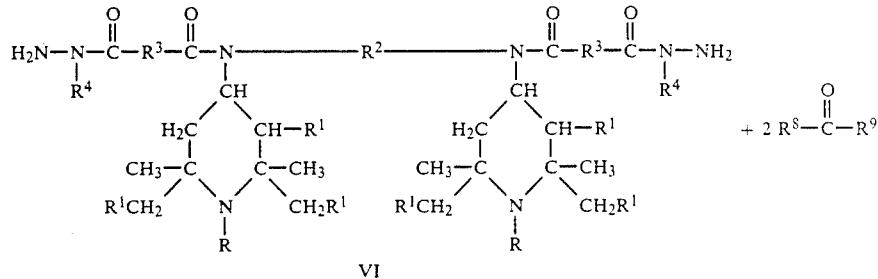

$R, R^1, R^2, R^3$ and $R^4$ are as broadly previously defined.

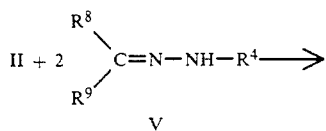

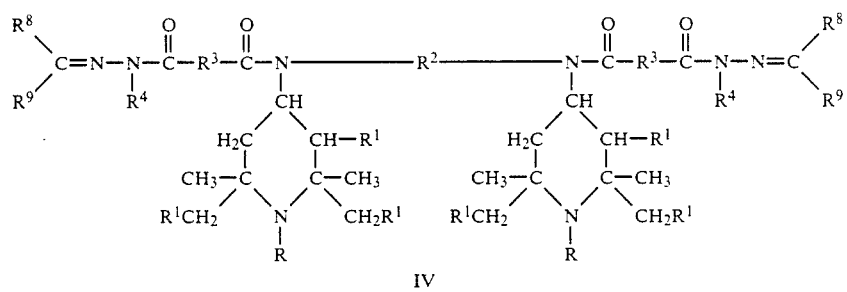

The reactions are carried out in dry, inert, polar solvents, such as methanol, ethanol, isopropanol or tetrahydrofuran (THF). Normally, the reactions are carried out at room temperature to 40° C. for the oxamic acid drivatives (i.e., the compound of Formula IV where $R^3$ is a direct bond). Additionally, the reactions require heating or refluxing to form the other amic acid derivatives.

Non-limiting examples of suitable Formula V hydrazones include acetone hydrazone, 2-butanone hydrazone, cyclohexanone hydrazone, acetophenone hydrazone, benzophenone hydrazone, acetone methylhydrazone, acetone ethylhydrazone, acetone isobutylhydrazone, 2-butanone cyclohexylhydrazone, cyclohexanone benzylhdyrazone, 2-pentanone cyclododecylhydrazone and 2-hexanone isopropylhydrazone.

Preparation of Substituted bis HALS Amic Acid Hydrazides

The novel Formula IV hydrazones, prepared by Method IB where $R^4$ is alkyl of 1 to 8 carbons, aralkyl of 7 to 12 carbons or cycloalkyl of 5 to 12 carbons, may be hydrolyzed to afford substituted hydrazides, designated as Formula VI (i.e., Formula I where $R^5$ is $H_2N-$). The method is illustrated by the following equation:

The hydrolysis reaction is carried out in water or aqueous alcohol. It can be catalyzed by a small amount of sulfuric acid or hydrochloric acid. However, if an acid catalyst is used, the reaction mixture should be neutralized before isolating the product. Preferably, the hydrolysis is carried out on the acetone derivative or the 2-butanone derivative (i.e., Formula IV where $R^8$ is methyl and $R^9$ is methyl or ethyl) wherein the aqueous reaction mixture is heated and the acetone or 2-butanone is distilled off as it forms.

III. Preparation of Carbamoyl and Thiocarbamoyl Derivatives

Method A

The novel carbamoyl and thiocarbamoyl derivatives of Formula I, where $R^5$ is $(R^6)(R^7)N-$, $R^6$ is hydrogen and $R^7$ is mono-substituted carbamoyl or mono-substituted thiocarbamoyl, designated as Formula VII, may be prepared by reacting the Formula VI bis HALS amic acid hydrazides with isocyanates or isothiocyanates, designated as Formula VIII, as indicated by the following reaction equation:

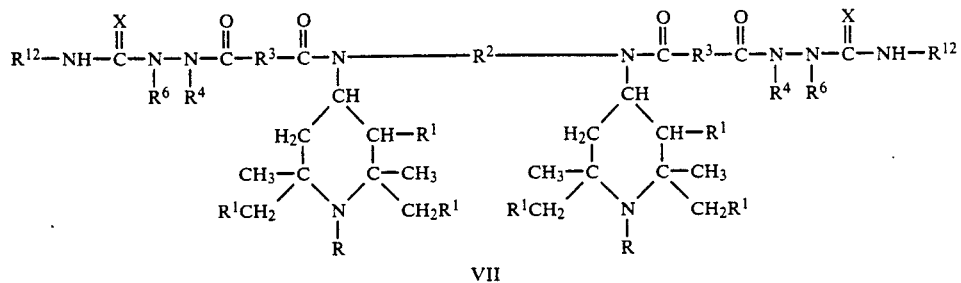

VII

X is O or S and R, $R^1$, $R^2$, $R^3$ and $R^4$ are as broadly previously defined, $R^6$ is hydrogen and $R^{12}$ is alkyl of 1 to 20 carbons, alkenyl of 3 to 12 carbons, cycloalkyl of 5 to 12 carbons, substituted or unsubstituted aralkyl of 7 to 15 carbons or substituted or unsubstituted aryl of 6 to 14 carbons, where the substitutents for the aralkyl and aryl groups are at least one of chlorine, bromine, alkyl of 1 to 8 carbons, alkenyl of 3 to 8 carbons or alkoxy of 1 to 8 carbons.

The reaction is carried out in polar aprotic solvents, such as diethyl ether, methyl t-butyl ether, THF or dimethylformamide (DMF). The reaction normally occurs at room temperature, but gentle heating of the reaction mixture may be used to assure that the reactants react completely.

Non-limiting examples of suitable isocyanates include allyl, benzyl, n-butyl, t-butyl, cyclohexyl, ethyl, isopropyl, 4-methoxyphenyl, methyl, octadecyl, I-naphthyl, phenyl, o-, m- and p-tolyl and dimethyl-m-isopropenylbenzyl isocyanates.

Non-limiting examples of suitable isothiocyanates include allyl, benzyl, 4-bromophenyl, n-butyl, t-butyl, 3-chlorophenyl, cyclohexyl, ethyl, methyl, 1-naphthyl, t-octyl, phenethyl, phenyl, propyl, o- and p-tolyl isothiocyanates.

Method B

The novel carbamoyl derivatives of Formula I, where $R^5$ is $(R^6)(R^7)N-$, $R^6$ is hydrogen and $R^7$ is di-substituted carbamoyl, designated as Formula IX, may be prepared by reacting the Formula VI bis HALS amic acid hydrazides with N,N-di-substituted carbamoyl chlorides, designated as Formula X, as indicated by the following reaction equation:

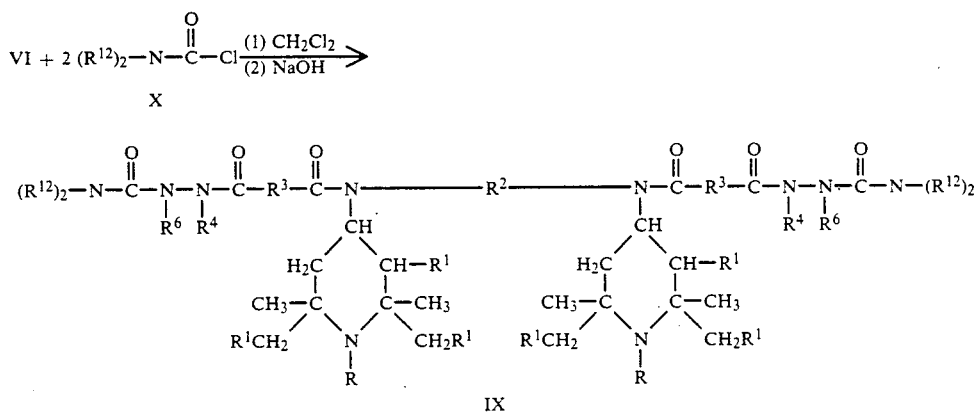

IX

R, $R^1$, $R^2$, $R^3$ and $R^4$ are as previously broadly defined, $R^6$ is hydrogen and $R^{12}$ is alkyl of 1 to 20 carbons, alkenyl of 3 to 12 carbons, cycloalkyl of 5 to 12 carbons, substituted or unsubstituted aralkyl of 7 to 15 carbons or substituted or unsubstituted aryl of 6 to 14 carbons, where the substituents for the aralkyl and aryl groups are at least one of chlorine, bromine, alkyl of 1 to 8 carbons, alkenyl of 3 to 8 carbons and alkoxy of 1 to 8 carbons.

The reaction can be carried out at room temperature in non-polar solvents, such as methylene chloride or chloroform. If R is not an acyl, carbamoyl, alkoxy, cycloalkoxy or aryloxy carbonyl group, the hindered amine will act as an acid acceptor and the hydrochloride salt of IX will form. The Formula IX derivatives can be isolated by neutralizing the hydrochloride salt with dilute sodium hydroxide.

Non-limiting examples of suitable N,N-di-substituted carbamoyl chlorides include N,N-dimethylcarbamoyl chloride and N,N-diethylcarbamoyl chloride.

Method C

The novel carbamoyl and thiocarbamoyl derivatives of Formula I, where $R^5$ is $(R^6)(R^7)N-$, $R^4$ and $R^6$ are as previously broadly defined and $R^7$ is carbamoyl, thiocarbamoyl, mono-substituted or di-substituted carbamoyl or mono-substituted or di-substituted thiocarbamoyl, designated as Formula XI, may be prepared by reacting suitably substituted semicarbazides or thiosemicarbazides, designated as Formula XII, with the Formula II bis (half ester-half amides), as indicated by the following reaction equation:

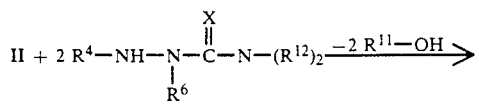

XII

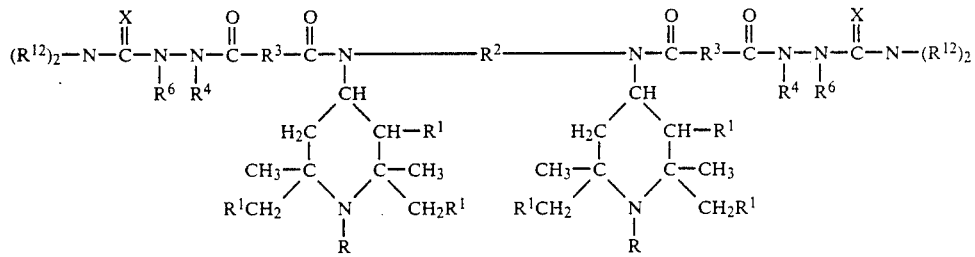

IX

X is O or S and R, $R^1$, $R^2$, $R^3$, $R^4$, $R^6$ and $R^{12}$ are as previously broadly defined and, in addition, $R^{12}$ may also be hydrogen. The reactions are preferably carried out in refluxing methanol or ethanol.

Non-limiting examples of suitable semicarbazides and thiosemicarbazides include semicarbazide, thiosemicarbazide, 4-phenylsemicarbazide, 4,4-diethylsemicarbazide, 1-methylsemicarbazide, 1-phenylsemicarbazide, 4,4-dimethylthiosemicarbazide, 4,4-diphenylthiosemicarbazide, 1-cyclohexyl-4-propylsemicarbazide and 1,2-dimethylsemicarbazide.

Preparation of Acyl Derivatives

Method A

The novel acyl derivatives of Formula I, where $R^5$ is $(R^6)(R^7)N$—, $R^6$ is as previously defined, $R^7$ is substituted or unsubstituted aliphatic acyl of 2 to 20 carbons, substituted or unsubstituted alicyclic acyl of 6 to 13 carbons, substituted or unsubstituted araliphatic acyl of 8 to 16 carbons or substituted or unsubstituted aromatic acyl of 7 to 20 carbons and designated as Formula XIII, may be prepared by reacting an acyl hydrazide, designated as Formula XIV with the Formula II bis (half ester-half amides), as indicated by the following reaction equation:

least one of chlorine, bromine, alkyl of 1 to 8 carbons, alkoxy of 1 to 8 carbons, phenoxy, cyano, hydroxy or epoxy.

The reactions are carried out by refluxing the Formula II bis (half ester-half amides) with approximately two equivalents of Formula XIV acyl hydrazide in a minimal amount of methanol or ethanol. The reactions may also be run neat by heating the two reagents into a melt above 80° C. for approximately 30 to 60 minutes.

Non-limiting examples of suitable acyl hydrazides include acetic, propionic, butyric, isobutyric, valeric, caproic, heptanoic, caprylic, decanoic, lauric, stearic and benzoic hydrazides, 3,5-di-t-butyl-4-hydroxybenzhydrazide and 3-(3,5-di-t-butyl-4-hydroxyphenyl)propionic acid hydrazide.

Method B

The novel Formula XIII acyl derivatives, where R, $R^1$, $R^2$, $R^3$, $R^4$, $R^6$ and $R^{13}$ are as previously broadly defined, may also be prepared by reacting approximately two moles of an acid chloride, designated as Formula XV, with one mole of a Formula VI bis HALS amic acid hydrazide, as indicated by the following reaction equation:

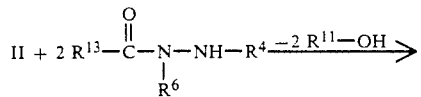

XIV

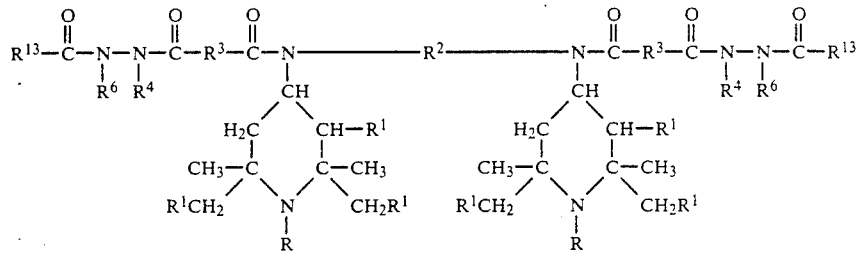

XIII

R, $R^1$, $R^2$, $R^3$, $R^4$ and $R^6$ are as previously broadly defined and $R^{13}$ is substituted or unsubstituted aliphatic of 1 to 19 carbons, substituted or unsubstituted alicyclic of 5 to 12 carbons, substituted or unsubstituted araliphatic of 7 to 15 carbons or substituted or unsubstituted aryl of 6 to 19 carbons, where the substituents are at

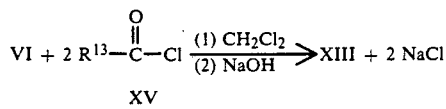 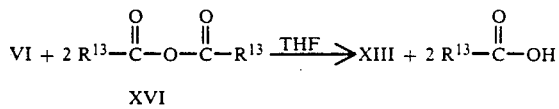

The reactions are carried out in inert, aprotic solvents such as methylene chloride, chloroform, diethyl ether, methyl t-butyl ether or THF. If the Formula VI hydrazide is unsubstituted on the hindered amines (i.e., R is hydrogen), the Formula VI hydrazide can act as its own acid acceptor and the Formula XIII acyl derivative hydrochloride salt will form. The Formula XIII acyl derivatives can be isolated by neutralizing the salt with a stronger base, such as dilute sodium hydroxide or dilute potassium hydroxide. Reacting the acid chlorides with the bis HALS amic acid hydrazides occurs very readily and, generally, there is some heat generated. Consequently, it is preferable to control the reaction temperature by cooling the reaction flask with a cold water or ice bath. The temperature can also be controlled by using a low boiling solvent, such as methylene chloride and a reflux condenser. Tertiary amines, such as pyridine and triethylamine may be used as acid acceptors if R is not hydrogen.

Non-limiting examples of suitable acid chlorides include acetyl chloride, acryloyl chloride, o-anisoyl chloride, benzoyl chloride, 3-bromobenzoyl chloride, t-butylacetyl chloride, 4-t-butylbenzoyl chloride, butyryl chloride, cinnamoyl chloride, crotonyl chloride, cyclohexanecarboxylic acid chloride, decanoyl chloride, 2,4-dichlorobenzoyl chloride, 2-ethylhexanoyl chloride, hexanoyl chloride, hydrocinnamoyl chloride, isobutyryl chloride, isovaleryl chloride, lauroyl chloride, methacryloyl chloride, 1-naphthoyl chloride, nonanoyl chloride, octanoyl chloride, phenoxyacetyl chloride, phenylacetyl chloride, propionyl chloride, o-, m- and p-toluoyl chlorides, trimethylacetyl chloride, undecanoyl chloride, valeryl chloride, 3,5-di-t-butyl-4-hydroxybenzoyl chloride and 3-(3,5-di-t-butyl-4-hydroxyphenyl)propionyl chloride.

Method C

The novel Formula XIII acyl derivatives, where R, $R^1$, $R^2$, $R^3$, $R^4$ and $R^6$ are as previously broadly defined and $R^{13}$ is aliphatic of 1 to 11 carbons or phenyl, may also be prepared by reacting the Formula VI bis HALS amic acid hydrazides with non-cyclic carboxylic acid anhydrides, designated as Formula XVI, as indicated by the following equation:

$R^{13}$ is aliphatic of 1 to 11 carbons or phenyl and R, $R^1$, $R^2$, $R^3$, $R^4$ and $R^6$ are as previously broadly defined.

The reactions are carried out by adding the anhydride to a slurry of the Formula VI bis HALS amic acid hydrazide in a polar aprotic solvent, such as THF, diethyl ether, methyl t-butyl ether or DMF. Normally, the reaction proceeds at room temperature, but warming after the initial exotherm assures that the reactants react completely.

Non-limiting examples of suitable non-cyclic anhydrides include acetic, butyric, isobutyric, propionic, valeric, hexanoic, heptanoic and benzoic anhydrides.

When the hindered amines are not acylated, for example, R is hydrogen, hydroxy, alkyl or aralkyl, the carboxylic acid $R^{13}$—C(=O)—OH, generated in the reaction, may form a salt, designated as Formula XIIIA, with the Formula XIII acyl derivatives, as indicated by the following reaction equation:

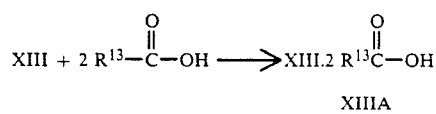

The Formula XIII free acyl derivatives may be regenerated from the carboxylic acid salt (Formula XIIIA) by neutralizing the carboxylic acid with aqueous sodium hydroxide or potassium hydroxide. The neutralization procedure is illustrated by the following equation:

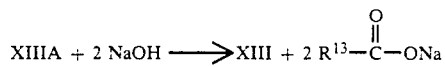

V. Preparation of Alkoxycarbonyl, Cycloalkoxycarbonyl and Aryloxycarbonyl Derivatives Method A The novel alkoxycarbonyl, cycloalkoxycarbonyl and aryloxycarbonyl derivatives of Formula I, where $R^5$ is $(R^6)(R^7)N$—, $R^6$ is as previously broadly defined and $R^7$ is alkoxycarbonyl of 2 to 13 carbons, cycloalkoxy carbonyl of 6 to 13 carbons or aryloxycarbonyl of 7 to 15 carbons and designated as Formula XVII, may be prepared by reacting alkyl, cycloalkyl or aryl carbazates, designated as Formula XVIII, with the Formula II bis (half ester-half amides), as indicated by the following reaction equation:

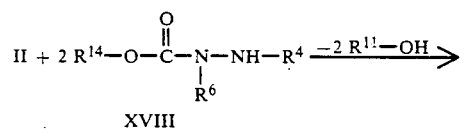

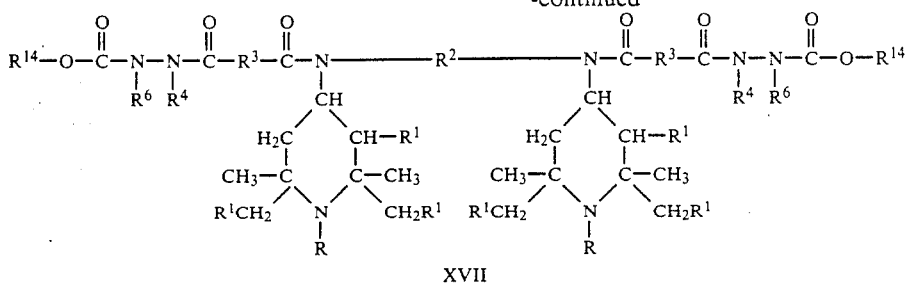

XVII

R, $R^1$, $R^2$, $R^3$, $R^4$ and $R^6$ are as previously broadly defined and $R^{14}$ is alkyl of 1 to 12 carbons, cycloalkyl of 5 to 12 carbons or aryl of 6 to 14 carbons.

The reactions are carried out by refluxing the Formula II bis(half ester-half amides) with approximately two equivalents of the Formula XVIII alkyl, cycloalkyl or aryl carbazate in a minimal amount of methanol or ethanol. The reactions may also be run neat by heating the two reagents into a melt above 80° C. for approximately 30 to 60 minutes.

Non-limiting examples of suitable carbazates include ethyl, methyl, propyl, isopropyl, butyl, isobutyl, cyclohexyl, cyclopentyl, cyclododecyl, phenyl, 3-ethylhexyl and octyl carbazates.

Method B

The Formula XVII alkoxycarbonyl, cycloalkoxycarbonyl and aryloxycarbonyl derivatives, where R, $R^1$, $R^2$, $R^3$, $R^4$, $R^6$ and $R^{14}$ are as previously broadly defined, may also be prepared by reacting approximately two moles of a chloroformate, designated as Formula XIX, with one mole of the Formula VI bis HALS amic acid hydrazide, as indicated by the following reaction equation:

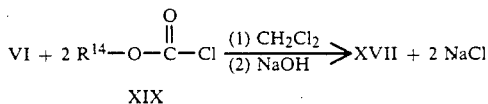

The reactions are run in inert, aprotic solvents, similar to the reaction of the Formula XV acid chloride with the Formula VI bis HALS amic acid hydrazide (see Method IVB). If the Formula VI bis HALS amic acid hydrazide is unsubstituted on the hindered amines (i.e., R is hydrogen), the Formula VI bis HALS amic acid hydrazide can act as its own acid acceptor and the hydrochloride salt of the Formula XVII derivatives will form. The Formula XVII derivatives can be isolated by neutralizing the salt with dilute sodium hydroxide.

Non-limiting examples of suitable chloroformates include methyl, ethyl, propyl, isopropyl, n-butyl, sec-butyl, isobutyl, n-amyl, 2-ethylhexyl, hexyl, cyclohexyl, phenyl, cycloheptyl, cyclododecyl and cyclooctyl chloroformates.

VI. Preparation of Imide and Amic Acid Derivatives

The novel amic acid derivatives of Formula I, where $R^5$ is $MOC(=O)-R^{10}-C(=O)-N(R^6)-$ and $R^6$ and M are each hydrogen and designated as Formula XX, may be prepared by reacting the Formula VI bis HALS amic acid hydrazides with cyclic anhydrides, designated as Formula XXI, as indicated by the following reaction equation:

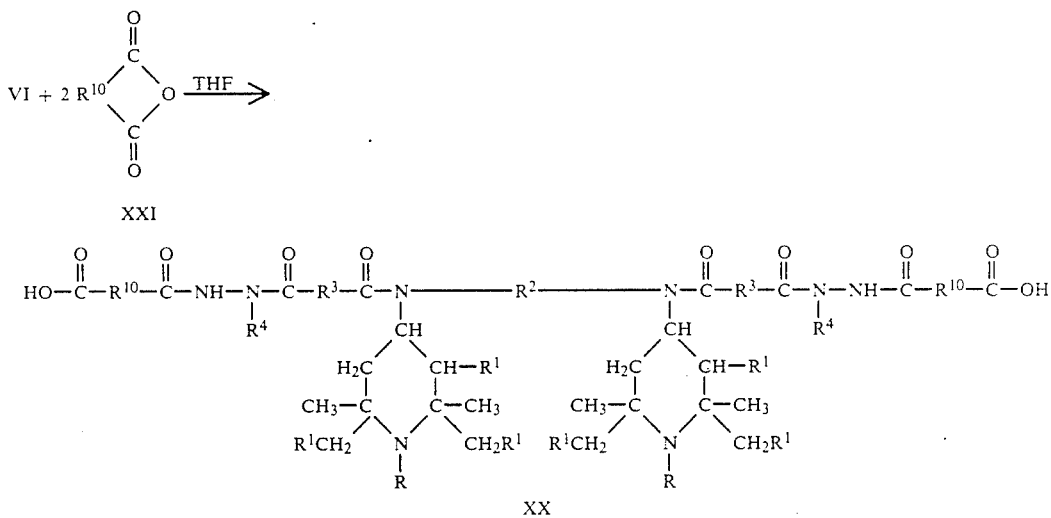

XX

R, $R^1$, $R^2$, $R^3$, $R^4$ and $R^{10}$ are as previously broadly defined.

The reactions are carried out in inert, polar aprotic solvents, such as THF, diethyl ether, methyl t-butyl ether or DMF. The reactions generally occur at room temperature, but gentle warming may be used to speed up the reaction or to assure that the reactants react completely.

Non-limiting examples of suitable cyclic anhydrides include 3,3-dimethylglutaric, 2-dodecen-1-ylsuccinic, 2-octadecen-1-ylsuccinic, 2-octen-1-ylsuccinic, 2-hexen-1-ylsuccinic, 2-dodecylsuccinic, 2-octadecylsuccinic, 2-octylsuccinic, 2-hexylsuccinic, succinic, itaconic, citraconic, maleic, phthalic, 4-methylphthalic, 1,8-naphthalic, glutaric, homophthalic, trimellitic, hexahydro-4-methylphthalic, hexahydrophthalic and methyl-4-norbornene-2,3-dicarboxylic anhydrides.

XV derivatives are then heated in one of the above solvents until imidization occurs.

The preparation of the imide derivatives is illustrated by the following reaction equations:

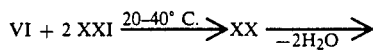

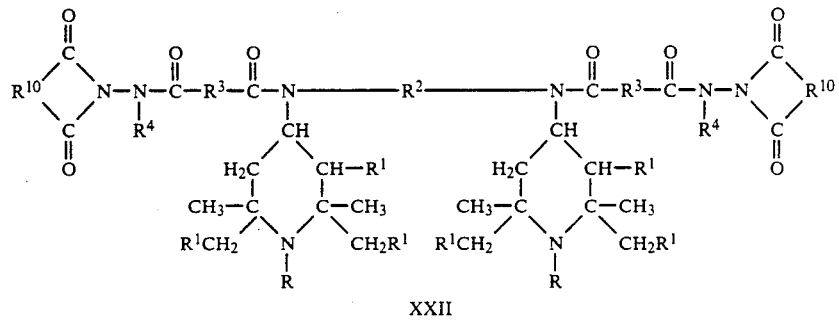

The Formula XV amic acid derivatives may be converted to the corresponding sodium, potassium or ammonium salts, i.e., Formula I where $R^5$ is $MOC(=O)-R^{10}-C(=O)-N(R^6)-$ and M is a sodium, potassium or ammonium ion, by neutralizing the Formula XV amic acid derivatives with sodium hydroxide, potassium hydroxide or ammonium hydroxide.

The novel imide derivatives of Formula I, where $R^5$ is $$\begin{array}{c} O \\ \| \\ C \\ R^{10} \diagdown \diagup \diagdown N- \\ C \\ \| \\ O \end{array}$$

and designated as Formula XXII, are prepared by reacting the Formula VI bis HALS amic acid hydrazides with Formula XXI cyclic anhydrides in inert, moderately high boiling solvents (b.p. 100°–200° C.). The Formula XX intermediate amic acid forms and, upon heating, the amic acid cyclizes with loss of water to form the Formula XXII imide. Preferably, the water is azeotropically distilled off from the reaction using solvents such as toluene, xylene or mesitylene. Other suitable solvents for the reaction include chlorobenzene, dichlorobenzene, dimethylformamide, N-methyl pyrrolidone or N-cyclohexyl pyrrolidone.

The Formula XXII imide derivatives may also be prepared in two steps by first preparing and isolating the Formula XV amic acid derivatives. The Formula Non-limiting examples of suitable cyclic anhydrides include the above list given for the preparation of the amic acid derivatives.

VII. Preparation of Alkyl, Hydroxyalkyl, Cycloalkyl, Aralkyl or Aryl Derivatives Method A The novel alkyl, hydroxyalkyl, cycloalkyl, aralkyl and aryl derivatives of Formula I, where $R^5$ is $(R^6)(R^7)N-$, $R^6$ is as previously broadly defined and $R^7$ is hydrogen, lower alkyl of 1 to 4 carbons or hydroxyalkyl of 2 to 6 carbons, designated as Formula XXIII, may be prepared by reacting the Formula II bis(half ester-half amides) with mono-, di- or tri-substituted hydrazines, designated as Formula XXIV, as indicated by the following reaction equation:

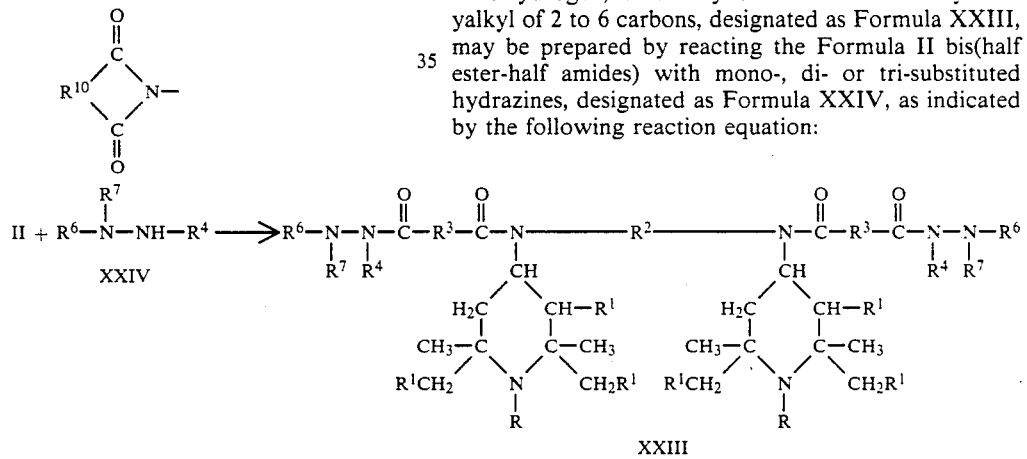

$R$, $R^1$, $R^2$, $R^3$, $R^4$ and $R^6$ are as previously broadly defined and $R^7$ is hydrogen, lower alkyl of 1 to 4 carbons or hydroxyalkyl of 2 to 6 carbons.

Preferably, the reaction is carried out in methanol or ethanol using a slight excess of the substituted hydrazine. The reaction generally proceeds at room temperature with the Formula II oxamate esters (i.e., $R^3$ is a direct bond) and generally requires heating or refluxing with the other Formula II amic acid esters.

Non-limiting examples of suitable substituted hydrazines include methyl, ethyl, propyl, isopropyl, butyl, sec-butyl, amyl, t-amyl, hexyl, heptyl, octyl, 2-ethylhexyl, cyclopentyl, cyclohexyl, cycloheptyl, cyclooctyl, cyclododecyl, 4-t-butylcyclohexyl, 2-methylcyclohexyl, benzyl, alpha-methylbenzyl, alpha,alpha-dimethylbenzyl, phenethyl, phenyl, 1,1-dimethyl, 1,2- dimethyl, 1,1-diethyl, 1,2-diethyl, 2-hydroxyethyl, 1-methyl-1-phenyl, o-, m-, and p-tolyl hydrazines.

VIII. Preparation of Miscellaneous Substituted Derivatives

The novel Formula XXIII compounds, where $R^7$ is hydrogen and $R^6$ is as previously broadly defined, can be reacted with the Formula VIII isocynates or the Formula VIII isothiocyanates, according to Preparative Method IIIA, to yield Formula VII compounds where $R^6$ is alkyl of 1 to 12 carbons, cycloalkyl of 5 to 12 carbons, aralkyl of 7 to 12 carbons or aryl of 6 to 14 carbons.

In addition, the Formula XXIII compounds may also be reacted with the Formula X N,N-di-substituted carbamoyl chlorides to afford the Formula IX compounds where $R^6$ need not be hydrogen, according to Preparative Method IIIB.

Utility

The novel stabilizers of this invention are very effective additives for stabilizing polymeric compositions which are normally subject to thermal, oxidative or actinic light degradation. At times it may be beneficial to add other additives which will act as synergists with the hindered amine light stabilizing groups.

The novel stabilizers of this invention can be blended with various polymeric compositions in high concentrations to form masterbatches which can then be blended with additional polymer of either the same or different type.

The amount of stabilizer used to stabilize the polymeric composition will depend on the particular polymer system to be stabilized, the degree of stabilization desired and the presence of other stabilizers in the composition. Normally, it is advisable to have about 0.01% to about 5% by weight of the 2,2,6,6-tetraalkylpiperidine moiety present in the polymeric composition. An advantageous range is from about 0.05% to about 2% by weight of the 2,2,6,6-tetraalkylpiperidine portion of the molecule in the final composition. In most cases, about 0.1% to about 0.5% by weight is sufficient.

Non-limiting examples of polymeric compositions which may be stabilized by these novel hindered amine light stabilizers include:

(1) Polyolefins, such as high, low and linear low density polyethylenes, which may be optionally crosslinked, polypropylene, polyisobutylene, poly(methylbutene-1), polyacetylene and, in general, polyolefins derived from monomers having from 2 to about 10 carbon atoms, and mixtures thereof.

(2) Polyolefins derived from diolefins, such as polybutadiene and polyisoprene.

(3) Copolymers of mono or diolefins, such as ethylene-propylene, propylene-butene-1, propylene-isobutylene and ethylene-butene-1 copolymer.

(4) Terpolymers of ethylene and propylene with dienes (EPDM), such as butadiene, hexadiene, dicyclopentadiene and ethylidene norbornene.

(5) Copolymers of alpha-olefins with acrylic acid or methacrylic acids or their derivatives, such as ethylene-acrylic acid, ethylene-methacrylic acid and ethylene-ethyl acrylate copolymers.

(6) Styrenic polymers, such as polystyrene (PS) and poly(p-methylstyrene).

(7) Styrenic copolymers and terpolymers, such as styrene-butadiene (SBR), styrene-allyl alcohol and styrene-acrylonitrile (SAN), styrene-acrylonitrile-methacrylate terpolymer, styrene-butadiene-styrene block copolymers (SBS), rubber modified styrenics, such as styrene-acrylonitrile copolymers modified with acrylic ester polymer (ASA), graft copolymers of styrene on rubbers, such as polybutadiene (HIPS), polyisoprene or styrene-butadiene-styrene block copolymers (Stereon TM products available from Firestone Synthetic Rubber and Latex Co.), graft copolymers of styrene-acrylonitrile on rubbers, such as butadiene (ABS), polyisoprene or styrene-butadiene-styrene block copolymers, graft copolymers of styrene-methyl methacrylate on rubbers, such as polybutadiene (MBS), butadiene-styrene radial block copolymers (e.g., KRO 3 TM of Phillips Petroleum Co.), selectively hydrogenated butadiene-styrene block copolymers (e.g., Kraton G TM from Shell Chemical Co.) and mixtures thereof.

(8) Polymers and copolymers derived from halogen-containing vinyl monomers, such as poly(vinyl chloride), poly(vinyl fluoride), poly(vinylidene chloride), poly(vinylidene fluoride), poly(tetrafluoroethylene) (PTFE), vinyl chloride-vinyl acetate copolymers, vinylidene chloride vinyl acetate copolymers and ethylenetetrafluoroethylene copolymers.

(9) Halogenated rubbers, such as chlorinated and/or brominated butyl rubbers or polyolefins and fluoroelastomers.

(10) Polymers and copolymers derived from alpha, beta-unsaturated acids, anhydrides, esters, amides and nitriles or combinations thereof, such as polymers or copolymers of acrylic and methacrylic acids, alkyl and/or glycidyl acrylates and methacrylates, acrylamide and methacrylamide, acrylonitrile, maleic anhydride, maleimide, the various anhydride containing polymers and copolymers described in this disclosure, copolymers of the polymers set forth in this paragraph and various blends and mixtures thereof, as well as rubber modified versions of the polymers and copolymers set forth in this paragraph.

(11) Polymers and copolymers derived from unsaturated alcohols or their acylated derivatives, such as poly(vinyl alcohol), poly(vinyl acetate), poly(vinyl stearate), poly(vinyl benzoate), poly(vinyl maleate), poly(vinyl butyral), poly(allyl phthalate), poly(allyl diethylene glycol carbonate) (ADC), ethylene-vinyl acetate copolymer and ethylene-vinyl alcohol copolymers.

(12) Polymers and copolymers derived from unsaturated amines, such as poly(allyl melamine).

(13) Polymers and copolymers derived from epoxides, such as polyethylene oxide, polypropylene oxide and copolymers thereof, as well as polymers derived from bis-glycidyl ethers.

(14) Poly(phenylene oxides), poly(phenylene ethers) and modifications thereof containing grafted polystyrene or rubbers, as well as their various blends with polystyrene, rubber modified polystyrenes or nylon.

(15) Polycarbonates and especially the aromatic polycarbonates, such as those derived from phosgene and bisphenols, such as bisphenol-A, tetrabromobisphenol-A and tetramethylbisphenol-A.

(16) Polyesters derived from dicarboxylic acids and diols and/or hydroxycarboxylic acids or their corresponding lactones, such as polyalkylene phthalates (e.g., polyethylene terephthalate (PET), polybutylene terephthalate (PBT), and poly (1.4-dimethylcyclohexane terephthalate) or copolymers thereof) and polylactones, such as polycaprolactone.

(17) Polyarylates derived from bisphenols (e.g., bisphenol-A) and various aromatic acids, such as isophthalic and terephthalic acids or mixtures thereof.

(18) Aromatic copolyestercarbonates having carbonate as well as ester linkages present in the backbone of the polymers, such as those derived from bisphenols, iso- and terephthaloyl chlorides and phosgene.

(19) Polyurethanes and polyureas.

(20) Polyacetals, such as polyoxymethylenes and polyoxymethylenes which contain ethylene oxide as a comonomer.

(21) Polysulfones, polyethersulfones and polyimidesulfones.

(22) Polyamides and copolyamides which are derived from diamines and dicarboxylic acids and/or from aminocarboxylic acids or the corresponding lactones, such as the following nylons: 6, 6/6, 6/10, 11 and 12.

(23) Polyimides, polyetherimides, polyamideimides and copolyetheresters.

(24) Cross-linked polymers which are derived from aldehydes on the one hand and from phenols, ureas and melamine on the other hand, such as phenol-formaldehyde, urea-formaldehyde and melamine-formaldehyde resins.

(25) Alkyl resins, such as glycerolphthalic acid resins and mixtures thereof with melamine-formaldehyde resins.

(26) Blends of vinyl monomers and unsaturated polyester resins which are derived from copolyesters of saturated and unsaturated dicarboxylic acids with polyhydric alcohols, as well as from vinyl compounds (crosslinking agents) and also halogen-containing, flame resistant modifications thereof.

(27) Natural polymers, such as cellulose and natural rubber, as well as the chemically modified homologous derivatives thereof, such as cellulose acetates, cellulose propionate, cellulose butyrate and the cellulose ethers, such as methyl and ethyl cellulose.

In addition, the novel stabilizers of this invention may be used to stabilize various combinations or blends of the above polymers or copolymers. They are particularly useful for stabilizing polyolefins, acrylic coatings, styrenics, rubber modified styrenics, poly(phenylene oxides) and their various blends with styrenics, rubber-modified styrenics or nylon.

The novel hindered amine light stabilizers of this invention can be used together with other additives to further enhance the properties of the finished polymer. Examples of other additives that can be used in conjunction with the stabilizers of this invention include antioxidants, such as alkylated monophenols, alkylated hydroquinones, hydroxylated thiodiphenyl ethers, alkylidene-bisphenols, hindered phenolic benzyl compounds, acylaminophenols, esters of 3-(3,5-di-t-butyl-4-hydroxyphenyl)propionic acid, esters of 3-(5-t-butyl-4-hydroxy-3-methylphenyl)propionic acid, 3-(3,5-di-t-butyl-4-hydroxyphenyl)propionic acid amides; UV absorbers and light stabilizers, such as 2-(2'-hydroxyphenyl)-2H-benzotriazoles, 2-hydroxybenzophenones, benzylidene malonate esters, esters of substituted or unsubstituted benzoic acids, diphenyl acrylates, nickel chelates, oxalic acid diamides, other hindered amine light stabilizers, other additives, such as metal deactivators, phosphites and phosphonites, peroxide decomposers, fillers and reinforcing agents, plasticizers, lubricants, corrosion and rust inhibitors, emulsifiers, mold release agents, carbon black, pigments, fluorescent brighteners, both organic and inorganic flame retardants and non-dripping agents, melt flow improvers and antistatic agents. Numerous examples of suitable additives of the above type are given in Canadian Patent 1,190,038.

The following examples are presented to provide a more detailed explanation of the present invention and are intended as illustrations and not limitations of the invention.

Starting Materials 1,6-Hexamethylene triacetonediamine was obtained from Huls America, Inc. Ethyl oxalyl chloride, ethyl succinyl chloride and ethyl malonyl chloride were purchased from Aldrich Chemical Co. Ethyl adipoyl chloride and ethyl azelaoyl chloride were prepared from thionyl chloride and adipic acid monoethyl ester and azelaic acid monoethyl ester, respectively, which were purchased from Aldrich Chemical Co. n-Butyl isocyanate, octadecyl isocyanate and hexahydro-4-methylphthalic anhydride were also purchased from Aldrich. Dodecylsuccinic anhydride was purchased from Humphrey Chemicals. TMI (dimethyl-m-isopropenylbenzyl isocyanate) was obtained from American Cyanamid Company. 85% Hydrazine hydrate was purchased from J. T. Baker Chemical Co. Irganox ™ 1076 (octadecyl 3,5-di-t-butyl-4-hydroxyhydrocinnamate) was obtained from Ciba-Geigy Corp. UV-Chek ™ AM-340 (2,4-di-t-butylphenyl 3,5-di-t-butyl-4-hydroxybenzoate) was obtained from Ferro Corporation.

EXAMPLE I

Preparation of N,N'-Hexamethylenebis[N-(2,2,6,6-tetramethyl-4-piperidinyl)oxamic acid hydrazide]

A) Preparation of Diethyl N,N'-hexamethylenebis[N-(2,2,6,6-tetramethyl-4-piperidinyl)oxamate]

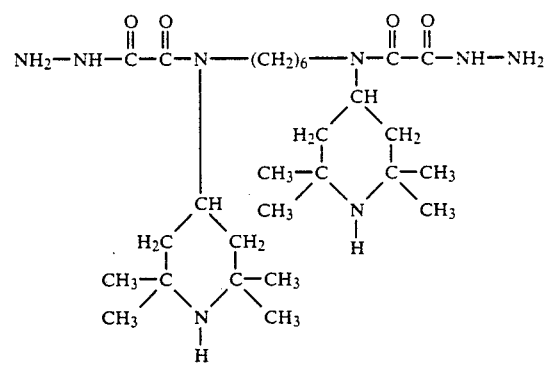

Into a 300 ml, 3-necked flask was introduced 1,6-hexamethylene triacetonediamine (19.7 g, 0.05 mole) and 200 ml of methylene chloride. The flask was equipped with a magnetic stirrer, a thermometer, a reflux condenser and a dropping funnel containing ethyl oxalyl chloride (14.0 g, 0.10 mole). The ethyl oxalyl chloride was added dropwise to the stirring diamine solution over 15 minutes while controlling the temperature between 20° C. and 30° C. with a cold water bath. After the addition was complete, the water bath was removed and the reaction was stirred for 3 hours at room temperature. The methylene chloride solution was added to a stirring solution of sodium carbonate (15 g) in 200 ml water. The mixture was stirred 5 minutes, transferred to a separatory funnel and the methylene chloride layer was separated. The methylene chloride layer was dried over anhydrous sodium sulfate, filtered and the methylene chloride was stripped off on a rotating evaporator under reduced pressure. The residue was a light brown viscous liquid weighing 32.9 g. The infrared spectrum of the product contained strong carbonyl bands at 1735 cm$^{-1}$ and 1650 cm$^{-1}$.

B) Preparation of N,N'-Hexamethylenebis[N-(2,2,6,6-tetramethyl-4-piperidinyl)oxamic acid hydrazide]

The residue from part A was dissolved in 100 ml of methanol and transferred to a 250 ml, 3-necked flask. The flask was equipped with a magnetic stirrer, a thermometer, a condenser and a dropping funnel containing 85% hydrazine hydrate (9.0 g, 0.15 mole). The hydrazine hydrate was added dropwise over about 5 minutes at 32° C. After the addition was complete, the reaction was stirred 1 hour and allowed to stand overnight. The next morning the reaction mixture was filtered to remove a small amount of insoluble material. The filtrate was then stripped of solvent. The sticky yellow residue was slurried in 150 ml of warm tetrahydrofuran (THF) until the residue turned into a fine white solid. The solid product was filtered off and air dried. The product weighed 31.7 g after drying and had a melting range of 185°–188° C. The infrared spectrum of the product had strong carbonyl bands at 1620 cm$^{-1}$ and 1670 cm$^{-1}$ and the ester band at 1735 cm$^{-1}$ in the oxamate had completely disappeared.

EXAMPLE II

Preparation of N,N'-Hexamethylenebis[N-(2,2,6,6-tetramethyl-4-piperidinyl)succinamic acid hydrazide]

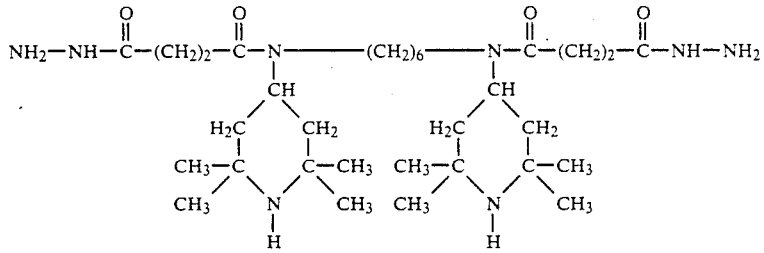

A) Diethyl N,N'-hexamethylenebis[N-(2,2,6,6-tetramethyl-4-piperidinyl)succinamate] was prepared according to the procedure of Example IA by adding ethyl succinyl chloride (16.5 g, 0.1 mole) to a solution of 1,6-hexamethylene triacetonediamine (19.7 g, 0.05 mole) in 200 ml of methylene chloride. After neutralizing and evaporating the solvent, a light tan solid was obtained weighing 30.9 g and melting at 110°–113° C. The infrared spectrum of the product contained strong carbonyl bands at 1730 cm$^{-1}$ and 1630 cm$^{-1}$.

B) N,N'-Hexamethylenebis[N-(2,2,6,6-tetramethyl-4-piperidinyl)succinamic hydrazide] was prepared by hydrazinolysis of 71.8 grams of a methanolic solution containing 21.4 g (0.033 mole) of the above succinamate with excess 85% hydrazine hydrate (12.9 g, 0.22 mole) according to the procedure of Example IB. The reaction was refluxed for three hours to complete the hydrazinolysis. Evaporation of the solvent afforded 27.8 g of a viscous yellow liquid which crystallized upon standing overnight (m.p. 81°–88° C.). The infrared spectrum (in CH$_2$Cl$_2$) had a strong, sharp carbonyl band at 1620 cm$^{-1}$ and a weaker carbonyl band at 1665 cm$^{-1}$. The ester band of the succinamate at 1730 cm$^{-1}$ had completely disappeared.

EXAMPLE III

Preparation of N,N'-Hexamethylenebis[N-(2,2,6,6-tetramethyl-4-piperidinyl)malonamic acid hydrazide]

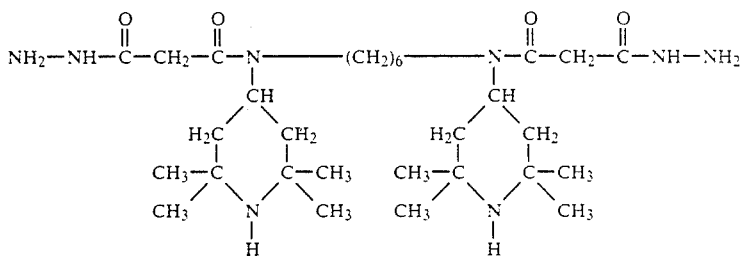

A) Diethyl N,N'-hexamethylenebis[N-(2,2,6,6-tetramethyl-4-piperidinyl)malonamate] was prepared according to the procedure of Example IA by adding ethyl malonyl chloride (15.06 g, 0.1 mole) to a solution of 1,6-hexamethylene triacetonediamine (19.7 g, 0.05 mole) in 200 ml of methylene chloride. After neutralizing and evaporating the solvent, a brown viscous liquid (28.5 g) was obtained. The infrared spectrum of the residue contained strong carbonyl bands at 1735 cm$^{-1}$ and 1640 cm$^{-1}$.

B) N,N'-Hexamethylenebis[N-(2,2,6,6-tetramethyl-4-piperidinyl)malonamic hydrazide] was prepared by hydrazinolysis of a solution of 28.5 g (0.05 mole) of the above malonamate in 75 ml of methanol with excess 54% hydrazine hydrate (11.85 g, 0.2 mole) according to the procedure of Example IB. After refluxing the methanolic reaction mixture for three hours, infrared spectroscopy indicated the ester group was completely converted to the hydrazide. The methanol was removed by evaporation and the product was dissolved in methylene chloride, washed with water, dried over anhydrous sodium sulfate and re-isolated by evaporating the methylene chloride. The product was a yellow viscous liquid and weighed 27.0 g. The infrared spectrum contained strong carbonyl bands at 1620 cm$^{-1}$ and 1670 cm$^{-1}$.

EXAMPLE IV

Preparation of

N,N'-Hexamethylenebis[N-(2,2,6,6-tetramethyl-4-piperidinyl)adipamic acid hydrazide]

EXAMPLE V

Preparation of
N,N'-Hexamethylenebis[N-(2,2,6,6-tetramethyl-4-piperidinyl)azelamic acid hydrazide]

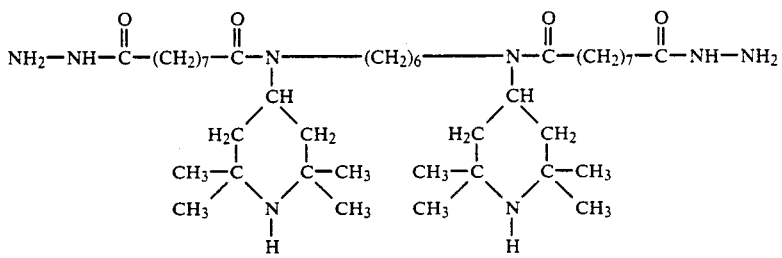

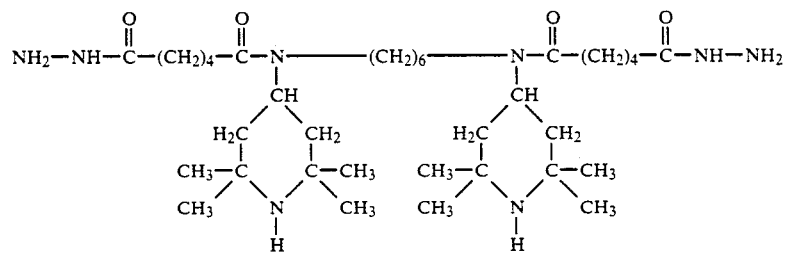

A) Diethyl N,N'-hexamethylenebis[N-(2,2,6,6-tetramethyl-4-piperidinyl)adipamate] was prepared according to the procedure of Example IA from monoethyl adipoyl chloride (9.2 g, 0.05 mole) and 1,6-hexamethylene triacetonediamine (9.9 g, 0.025 mole) in 125 ml of methylene chloride. After neutralizing and evaporating the solvent, a light brown viscous liquid (17.0 g) was obtained. The infrared spectrum of the residue contained strong carbonyl bands at 1735 cm$^{-1}$ and 1630 cm$^{-1}$.

B) N,N'-Hexamethylenebis[N-(2,2,6,6-tetramethyl-4-piperidinyl)adipamic acid hydrazide] was prepared by hydrazinolysis of a solution of 27.0 g (0.025 mole) of the above adipamate in 40 ml of methanol with excess 54% hydrazine hydrate (6.0 g, 0.1 mole) according to the procedure of Example IB. The methanolic solution was refluxed 5 hours to complete the hydrazinolysis. The reaction mixture was quenched and the product was isolated according to the procedure of Example IIIB. After evaporating the methylene chloride, the product obtained was a light brown viscous semisolid (17.05 g). The infrared spectrum of the product contained strong carbonyl bands at 1620 cm$^{-1}$ and 1660 cm$^{-1}$.

A) Diethyl N,N'-hexamethylenebis[N-(2,2,6,6-tetramethyl-4-piperidinyl)azelamate] was prepared according to the procedure of Example IA from monoethyl azelaoyl chloride (3.8 g, 0.017 mole) and 1,6-hexamethylene triacetonediamine (3.5 g, 0.009 mole) in 70 ml of methylene chloride. After neutralizing and evaporating the solvent, a light brown viscous liquid (6.45 g) was obtained. The infrared spectrum of the product contained strong carbonyl bands at 1735 cm$^{-1}$ and 1625 cm$^{-1}$.

B) N,N'-Hexamethylenebis[N-(2,2,6,6-tetramethyl-4-piperidinyl)azelamic acid hydrazide] was prepared by hydrazinolysis of a solution of 6.45 g (0.0085 mole) of the above azelamate in 40 ml of methanol with excess 54% hydrazine hydrate (3.35 g, 0.056 mole) according to the procedure of Example IIB. The methanolic solution was refluxed 5 hours to complete the hydrazinolysis. The reaction mixture was quenched and the product was isolated according to the procedure of Example IIIB. After evaporating the methylene chloride, the product weighed 6.6 g and was a yellow viscous liquid. The infrared spectrum of the product contained strong carbonyl bands at 1620 cm$^{-1}$ and 1660 cm$^{-1}$.

EXAMPLE VI

Reaction of
N,N'-Hexamethylenebis[N-(2,2,6,6-tetramethyl-4-piperidinyl)oxamic acid hydrazide] with
Dodecylsuccinic Anhydride N,N'-hexamethylenebis[N-(2,2,6,6-tetramethyl-4-piperidinyl)oxamic acid hydrazide]

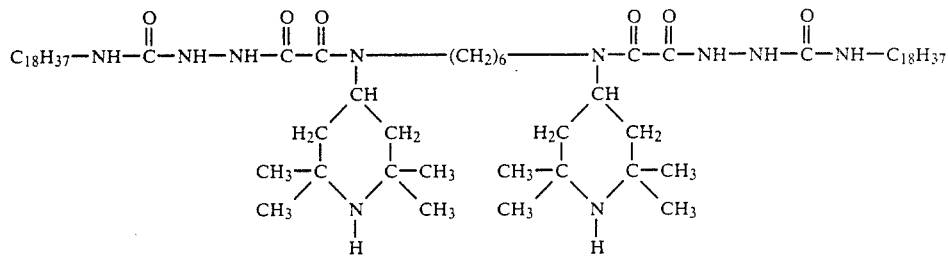

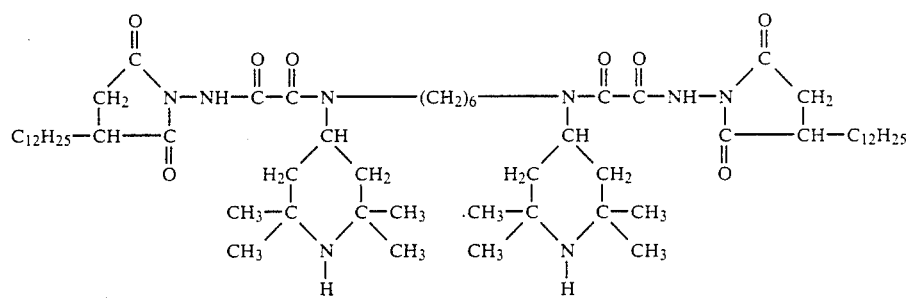

A solution of dodecylsuccinic anhydride (28.2 g, 0.105 mole) in 200 ml of xylene was heated in a 500 ml, 3-necked flask equipped with a magnetic stirrer, a thermometer and a Dean Stark trap containing a reflux condenser. When the solution temperature reached approximately 120° C., 14.2 g of the bis hydrazide from Example IB was added over 5 minutes. The hydrazide readily dissolved and the reaction was heated to reflux. The reaction mixture was azeotropically distilled for 1 hour, cooled to 130° C. and another 14.2 g of the bis HALS oxalyl hydrazide was added. The reaction mixture was again heated to reflux and azeotropically distilled an additional 2 hours. A total of 1.2 ml of water was collected in the Dean Stark trap (the theoretical amount of water was 1.8 ml). The xylene solution was cooled to 80° C. and was transferred to a 1 liter flask. The xylene was then stripped off on a rotating evaporator under reduced pressure. The residue was cooled to a brittle solid over dry ice, shattered and scraped out of the flask. The solidified residue was pulverized with a motor and pestle and air dried in a hood overnight. The produce weighed 47.4 g and had a melting range of 150°–173° C. The infrared scan contained carbonyl bands at 1725 cm$^{-1}$ (imide), 1655 cm$^-$ (amic acid) and 1565 cm$^{-1}$. The product was a mixture of the dodecylsuccinimide and dodecylsuccinamic acid derivative of N,N'-hexamethylenebis[N-(2,2,6,6-tetramethyl-4-piperidinyl)oxamic acid hydrazide]

Into a 250 ml, 3-necked flask was introduced the bis hydrazide from Example IB (14.2 g, 0.025 mole) and 125 ml of THF. The flask was equipped with a magnetic stirrer, a thermometer, a reflux condenser and a dropping funnel containing octadecyl isocyanate (14.8 g, 0.05 mole). The isocyanate was added dropwise over 5 minutes to the stirring hydrazide slurry. There was a slight exotherm and the temperature slowly rose from room temperature to 30° C. over 30 minutes, during which most of the solid material dissolved. The reaction was stirred 1 hour, warmed to 50° C. in a water bath and stirred an additional 2 hours at 40°–50° C. The hazy solution was filtered to remove a small amount of insoluble material. The filtrate was concentrated on a rotating evaporator under reduced pressure. A heat gun was used to remove the last traces of solvent. The residue was then cooled over dry ice to form a brittle glass. The brittle glass was shattered, scraped out of the flask and pulverized into a white powder with a mortar and pestle. After air drying overnight in a hood, the product weighed 22.5 g and had a melting range of 95°–102° C. The infrared spectrum of the product contained a broad, moderate carbonyl band at 1700 cm$^{-1}$ and strong, broad carbonyl bands at 1620 cm$^{-1}$ and 1535 cm$^{-1}$.

EXAMPLES VIII–XI

Reaction of
N,N'-Hexamethylenebis[N-(2,2,6,6-tetramethyl-4-piperidininyl)amic acid hydrazides] with Hexahydro-4-methylphthalic anhydride

A) Preparation of Bis Amic Acids

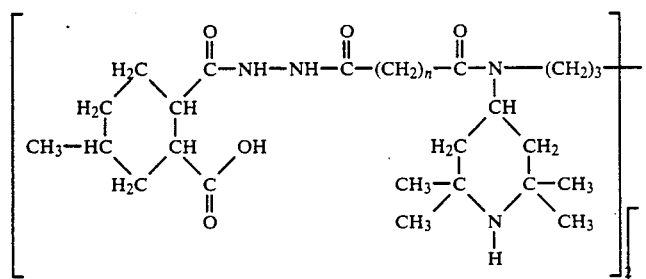

The amic acid derivatives were prepared by reacting the bis HALS amic acid hydrazides of Examples II–V with equal equivalents of hexahydro-4-methylphthalic anhydride in THF. The anhydride was added to the THF solution of the bis HALS amic acid hydrazide at room temperature. After a slight exotherm occurred (5°–10° C.) and white solid material formed, the reaction mixtures were warmed to 50° C. for 1 hour and then filtered. The infrared spectrum of the products had broad carbonyl bands in the 1615–1620 cm$^{-1}$ range. The results are summarized in Table I. The amic acid of Example XIA, a sticky solid after the THF was decanted, was not characterized.

B) Preparation of Bis Imides

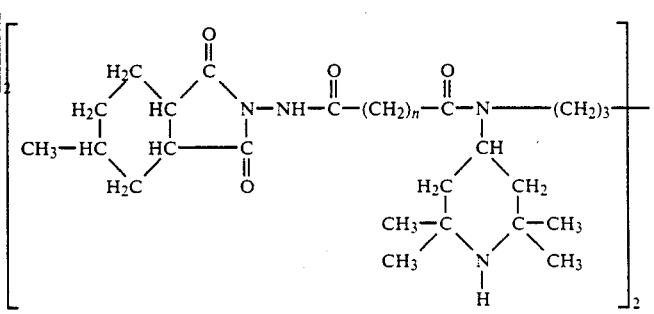

The amic acid derivatives prepared in step A were cyclized to the corresponding cyclic imides by refluxing the amic acid derivatives in xylene with the azeotropic removal of water until no additional water collected in the Dean Stark trap (1 to 1½ hours). Any insoluble material was filtered off from the hot xylene solutions and the products were isolated by stripping off the xylene on a rotating evaporator under reduced pressure. The infrared spectra of the products contained strong, sharp carbonyl bands at 1730–1735 cm$^{-1}$ and strong, broad carbonyl bands at 1615–1620 cm$^{-1}$. The results are summarized in Table II.

TABLE I

Reaction of N,N'-Hexamethylenebis[N-(2,2,6,6-tetramethyl-4-piperidinyl)amic acid hydrazides] with Hexahydro-4-methylphthalic Anhydride

| EXAMPLE | STARTING BIS HALS AMIC HYDRAZIDE | HYDRAZIDE (grams) | ANHYD. (grams) | YIELD (grams) | MELTING RANGE (°C.) | CARBONYL BANDS (cm$^{-1}$) |
|---|---|---|---|---|---|---|
| VIIIA | IIB | 12.45 | 6.72 | 19.5 | 152–157 | 1615 |
| IXA | IIIB | 8.9 | 5.05 | 11.7 | 156–160 | 1620–1550 (weak) |
| XA | IXB | 8.1 | 4.2 | 10.5 | 143–147 | 1620 |
| XIA | VB | 6.2 | 2.8 | | NOT ISOLATED | |

TABLE II

Imidization of the Amic Acid Derivatives in Refluxing Xylene

| EXAMPLE | AMIC ACID DERIVATIVE | REFLUX PERIOD (hours) | YIELD (grams) | MELTING RANGE (°C.) | CARBONYL BANDS (cm$^{-1}$) |
|---|---|---|---|---|---|
| VIIIB | VIIIA | 1½ | 16.0 | 104–108 | 1730 1615 |
| IXB | IXA | 1½ | 7.0 | 205–212 | 1730 1620 |
| XB | XA | 1½ | 8.8 | 110–114 | 1735 1615 |
| XIB | XIA | 1 | 6.2 | 98–104 | 1730 1620 |

EXAMPLES XII-XIV cm$^{-1}$ with shoulders around 1670 cm$^{-1}$ in their infrared spectra.

TABLE III

| | | Isocyanate Adducts of bis HALS Amic Acid Hydrazides | | | | | |
|---|---|---|---|---|---|---|---|
| EXAMPLE | STARTING AMIC ACID HYDRAZIDE | HYDRAZIDE (grams) | ISOCYANATE (RNCO) | GRAMS (RNCO) | YIELD (grams) | MELTING RANGE (°C.) | CARBONYL BANDS (cm$^{-1}$) |
| XII | IIB | 12.45 | n-Butyl | 4.0 | 14.3 | 110-114 | 1625 |
| | | | | | | | 1665 |
| XIII | IIIB | 8.9 | n-Butyl | 3.0 | 9.0 | 156-160 | 1630 |
| | | | | | | | 1660 |
| | | | | | | | 1690 |
| XIV | IVB | 8.1 | n-Butyl | 2.5 | 9.0 | 143-147 | 1630 |
| | | | | | | | 1670 |

Preparation of Isocyanate Adducts of N,N'-Hexamethylenebis-[N-(2,2,6,6-tetramethyl-4-piperidinyl)amic acid hydrazides]

EXAMPLE XV

Preparation of the Di-[N,N'-hexamethylenebis[N-(2,2,6,6-tetramethyl-4-piperidinyl)oxamic acid hydrazone] of 2-Butanone

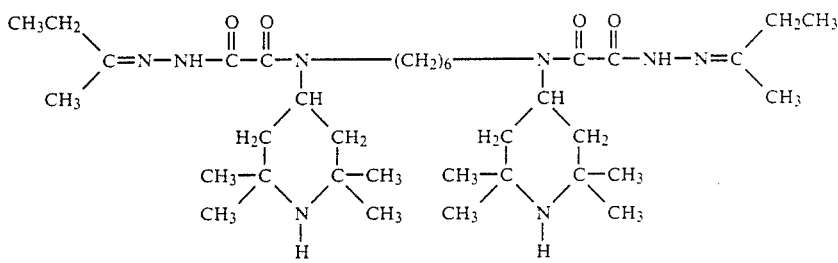

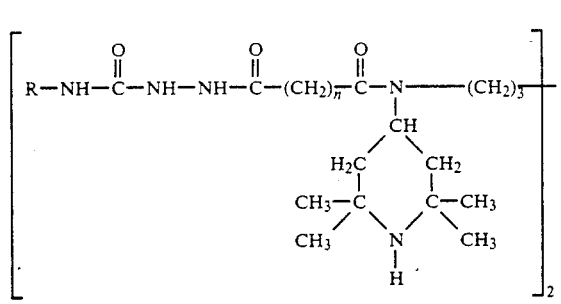

The isocyanate adducts were prepared by reacting the bis HALS amic acid hydrazides of Examples II-V with equal equivalents of the isocyanate in THF at room temperature. The reactions were stirred ½ hours at room temperature and then refluxed 1 hour (65° C.) to assure complete conversion of the amic acid hydrazides to the isocyanate adducts. The products were isolated by evaporating the THF on a rotating evaporator under reduced pressure. The residues were pulverized with a mortar and pestle and air dried in a hood overnight. The results are summarized in Table III. The products were characterized by strong carbonyl bands around 1630

Into a 250 ml, 3-necked flask was introduced N,N'-hexamethylenebis[N-(2,2,6,6-tetramethyl-4-piperidinyl)oxamic acid hydrazide] (11.33 g, 0.02 mole), 2-butanone (3.6 g, 0.05 mole) and 125 ml of xylene. The flask was equipped with a magnetic stirrer, a thermometer and a reflux condenser. The flask was heated in an oil bath to reflux gently at about 126° C. for 1 hour. After refluxing 1 hour, a Dean Stark trap was added to the apparatus and the reaction mixture was azeotropically distilled until no additional water collected in the Dean Stark trap (2 hours). The reaction mixture was cooled to 90° C. and transferred to a 500 ml round bottomed flask. The xylene was stripped off on a rotating evaporator under reduced pressure with the aid of a heat gun. The residue was scraped out of the flask and pulverized with a mortar and pestle into a straw-colored powder. The product weighed 8.8 g and had a melting range of 96°-100° C. The infrared spectrum of the product in methylene chloride contained strong, sharp carbonyl bands at 1670 and 1640 cm$^{-1}$.

EXAMPLE XVI

Preparation of the Di-[N,N'-hexamethylenebis[N-(2,2,6,6-tetramethyl-4-piperidinyl)succinamic acid hydrazone] of 2-Butanone

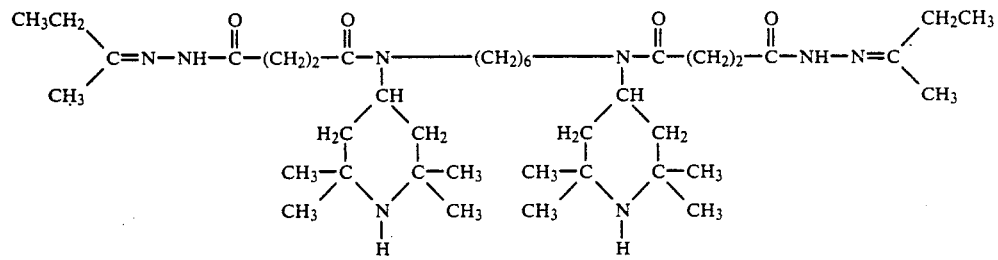

Di[N,N'-hexamethylenebis[N-(2,2,6,6-tetramethyl-4-piperidinyl)succinamic acid hydrazone] of 2-butanone was prepared by reacting N,N'-hexamethylenebis[N-(2,2,6,6-tetramethyl-4-piperidinyl)succinamic acid hydrazide] of Example II (12.45 g, 0.02 mole) with 2-butanone (3.6 g, 0.05 mole) according to the procedure of Example XV. The isolated product weighed 10.4 g and had a melting range of 50°-54° C. An infrared spectrum of the product in methylene chloride contained strong carbonyl bands at 1675 cm$^{-1}$ and 1630 cm$^{-1}$.

EXAMPLES XVII-XXXVIII

Preparation, Weathering and Evaluation of Tensile Bars Containing Bis HALS Amic Acid Hydrazides or their Derivatives Dry blends of Himont TM 6501 polypropylene, the bis HALS amic acid hydrazides or their derivatives and optionally a small amount of a hindered phenol antioxidant (Irganox TM 1076) were prepared in a polyethylene container (For compositions, see Table IV). The blends were shaken well to insure a good dispersion of the additives in the polypropylene. The blends were then extruded on a Brabender Prep Center Extruder Model No. 1340 having a 1 inch screw diameter with a length to diameter ratio of 25:1. The extruder was operated at a screw speed of 30 RPM and all the heating zones were controlled at 200° C. The first 100 grams of extrudate were used to purge out the extruder between runs and were discarded. The remaining extrudate was air-cooled and pelletized. The concentration of the 2,2,6,6-tetramethyl-4-piperidinyl group in the polypropylene was approximately 0.3%. The concentration of the Irganox TM 1076 (when used) was appproximately 0.25%. UV-Check TM AM-340 (when used) was included in some blends as a synergist at a concentration of 0.22%.

The pellets were injection molded in a Newbury 25 ton injection molding machine at 400° F. into $7\frac{3}{8}'' \times \frac{3}{4}'' \times \frac{1}{8}''$ tensile bars.

A control sample containing only Irganox TM 1076 was included for comparison. Control samples containing Irganox TM 1076 and Ciba-Geigy's commercial light stabilizers Chimasorb TM 944 or Tinuvin TM 770 were also included for comparison.

The tensile bars were placed in a QUV Accelerated Weathering Tester (Q Panel Company) for various exposure times. The QUV contained UV-B bulbs and operated with an 8 hour light cycle at 60° C. and a 4 hour condensation cycle at 50° C. Samples were placed in the QUV and withdrawn periodically at the same time of day. The tensile bars were pulled on an instrumented Instron according to ASTM Procedure 638. The minimum QUV exposure time required to obtain a brittle break in the Instron test was determined. A result was considered a brittle break when the tensile bar snapped before 15% elongation was obtained.

The QUV time interval required to generate spotting and clouding of the surface of the tensile bars was also noted.

The results are summarized in Table IV.

Tensile bars were also exposed to UV-A bulbs in a QUV under the same operating conditions for 60-80 days. The tensile bars were then pulled on the Instron. A brittle break was considered a failure and greater than 15% elongation was considered passing. These results are also summarized in Table IV.

The results indicate that the compounds of this invention are efficient light stabilizers for polypropylene and in most cases are considerably more efficient than the commercial light stabilizers against the degradative effects of both UV-A and UV-B light.

TABLE IV

Stabilization of Polypropylene with Bis HALS Amic Acid Hydrazides or their Derivatives

| Example No. | HALS Compound | HALS (grams) | Polypropylene (grams) | IRGANOX TM 1076 (grams) | UV-CHEK TM AM-340 (grams) | Days to Spotting in QUV-B | Days to Brittle Break in QUV-B | Pass-Fail 60 Days in QUV-A |
|---|---|---|---|---|---|---|---|---|
| XVII | I | 2.7 | 445 | — | — | >25 < 30 | >25 < 30 | Pass |
| XVIII | I | 2.7 | 445 | 1.1 | — | 35 | >35 < 40 | Pass |
| XIX | I | 2.7 | 445 | — | 1.0 | >70 | >70 | Pass** |
| XX | II | 3.0 | 445 | — | — | <30 | >25 < 30 | Pass |
| XXI | II | 3.0 | 445 | 1.1 | — | >30 < 35 | >30 < 35 | Pass** |
| XXII | II | 3.0 | 445 | — | 1.0 | >70 | >70 | Pass** |
| XXIII | VI | 5.1 | 445 | — | — | >35 | >20 < 25 | Pass |
| XXIV | VI | 5.1 | 445 | 1.1 | — | >35 | >25 < 30 | Pass |
| XXV | VI | 5.1 | 445 | — | 1.0 | >70 | >70 | Pass |
| XXVI | VII | 5.5 | 445 | — | — | >40 < 50 | >50 < 70 | Pass** |
| XXVII | VII | 5.5 | 445 | 1.1 | — | 70 | >70 | Pass |
| XXVIII | VII | 5.5 | 445 | — | 1.0 | >70 | >70 | Pass** |
| XXIX | XII | 3.9 | 445 | — | — | 30 | >25 < 30 | Fail |

TABLE IV-continued
Stabilization of Polypropylene with Bis HALS Amic Acid Hydrazides or their Derivatives

| Example No. | HALS Compound | HALS (grams) | Polypropylene (grams) | IRGANOX ™ 1076 (grams) | UV-CHEK ™ AM-340 (grams) | Days to Spotting in QUV-B | Days to Brittle Break in QUV-B | Pass-Fail 60 Days in QUV-A |
|---|---|---|---|---|---|---|---|---|
| XXX | XIII | 3.8 | 445 | — | — | 40 | >40 < 50 | Pass** |
| XXXI | XIV | 4.05 | 445 | — | — | 40 | >50 | Pass** |
| XXXII | XV | 3.2 | 445 | — | — | 20 | >20 < 25 | Fail |
| XXXIII | XV | 3.2 | 445 | 1.1 | — | >30 < 35 | >25 < 30 | Fail |
| XXXIV | XVI | 3.45 | 450 | — | — | >25 | >20 < 25 | NT |
| XXXV | XVI | 3.45 | 450 | 1.1 | — | 35 | >25 < 30 | NT |
| XXXVI | — | — | 445 | 1.1 | — | 6 | 5 | Fail |
| XXXVII | A | 2.85 | 445 | 1.1 | — | 35 | >15 < 25 | Fail* |
| XXXVIII | B | 2.30 | 445 | 1.1 | — | >35 | >20 < 25 | Fail* |

A = Chimasorb 944
B = Tinuvin 770
NT = Not tested
*failed at 50 days - passed at 40 days
**passed at 80 days in QUV-A

I claim:
1. A compound having a formula

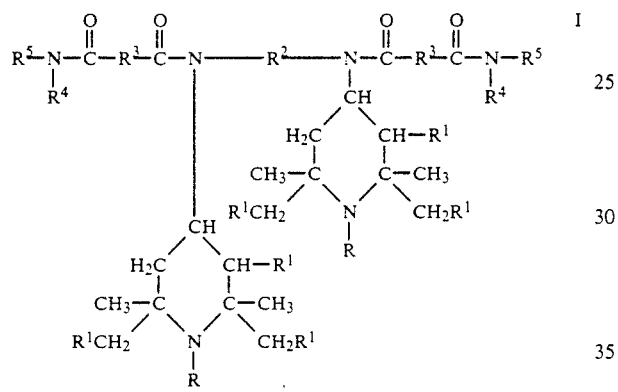

wherein
R is hydrogen; oxyl; hydroxy; substituted or unsubstituted aliphatic of 1 to 20 carbons; substituted or unsubstituted araliphatic of 7 to 22 carbons; substituted or unsubstituted aliphatic acyl of 2 to 20 carbons; substituted or unsubstituted alicyclic acyl of 6-13 carbons; substituted or unsubstituted aromatic acyl or 7 to 20 carbons, substituted or unsubstituted araliphatic acyl of 8 to 16 carbons; where the substituents for all of the above substituted groups are at least one of chlorine, bromine, alkyl of 1 to 8 carbons, alkoxy of 1 to 8 carbons, phenoxy, cyano, hydroxy or epoxy; alkoxycarbonyl of 2 to 9 carbons; cycloalkoxycarbonyl of 6 to 13 carbons; aryloxycarbonyl of 7 to 15 carbons; monosubstituted carbamoyl, where the substituent is alkyl of 1 to 20 carbons, cycloalkyl of 5 to 12 carbons, aralkyl of 7 to 15 carbons or aryl of 6 to 14 carbons; di-substituted carbamoyl, where the substituents are independently alkyl of 1 to 20 carbons, cycloalkyl of 5 to 12 carbons or aralkyl of 7 to 15 carbons; 2-cyanoethyl; hydroxyalkyl of 2 to 6 carbons; epoxyalkyl of 3 to 10 carbons or polyalkylene oxide of 4 to 30 carbons;

$R^1$ is hydrogen or lower alkyl of 1 to 4 carbons;
$R^2$ is an alkylene diradical of 2 to 18 carbons, an alkylene diradical of 4 to 18 carbons containing 1 to 2 —O—, —S— or —NH— heteroatoms, with the proviso that multiple heteroatoms must be separated from each other and the diradical ends by at least one carbon atom, a cycloalkylene diradical of 5 to 18 carbons, an alkylidenedicycloalkylene diradical of 14 to 18 carbons, a cycloalkylenedialkylene diradical of 14 to 18 carbons, an alkylene-dicycloalkylene diradical of 14 to 18 carbons, an arylene diradical of 6 to 12 carbons, an alkylenediarylene diradical of 13 to 18 carbons, an alkylidenediarylene diradical of 14 to 18 carbons or an aralkylene diradical of 8 to 18 carbons;

$R^3$ is a direct bond, an alkylene diradical of 1 to 14 carbons, an alkenylene diradical of 2 to 10 carbons, an oxydialkylene diradical of 4 to 10 carbons, a thiodialkylene diradical of 4 to 10 carbons or a substituted or unsubstituted o-, m- or p-phenylene diradical, where the substituents are lower alkyl of 1 to 6 carbons, hydroxy, bromine, chlorine, mercapto or lower alkylmercapto of 1 to 6 carbons;

$R^4$ is hydrogen, alkyl of 1 to 8 carbons, aralkyl of 7 to 12 carbons or cycloalkyl of 5 to 12 carbons;

$R^5$ is $(R^6)(R^7)N—$, $(R^8)(R^9)C=N—$, MOC(=O)—$R^{10}$—C(=O)—N($R^6$)— or

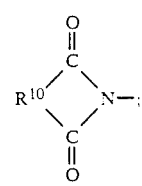

$R^6$ is hydrogen, alkyl of 1 to 12 carbons, cycloalkyl of 5 to 12 carbons, aralkyl of 7 to 12 carbons or aryl of 6 to 14 carbons;

$R^7$ is hydrogen; lower alkyl of 1 to 4 carbons; substituted or unsubstituted aliphatic acyl of 2 to 20 carbons, substituted or unsubstituted alicyclic acyl of 6 to 13 carbons, substituted or unsubstituted araliphatic acyl of 8 to 16 carbons, substituted or unsubstituted aromatic acyl of 7 to 20 carbons, where the substituents for the substituted acyl groups are at least one of chlorine, bromine, alkyl of 1 to 8 carbons, alkoxy of 1 to 8 carbons, phenoxy, cyano, hydroxy or epoxy; alkoxycarbonyl of 2 to 13 carbons; cycloalkoxycarbonyl of 6 to 13 carbons; aryloxycarbonyl of 7 to 15 carbons; hydroxyalkyl of 2 to 6 carbons; carbamoyl; thiocarbamoyl; mono-substituted carbamoyl or mono-substituted thiocarbamoyl, where the substituent is alkyl of 1 to 20 carbons, alkenyl of 3 to 12 carbons, cycloalkyl of 5 to 12 carbons, substituted or unsubstituted aralkyl of 7 to 15 carbons or substituted or unsubstituted aryl of 6 to 14 carbons; or di-substituted carbamoyl or di-substituted thiocarbamoyl, where the substituents are independently alkyl of 1 to 20 carbons, cycloalkyl of 5 to 12 carbons, substituted or unsubstituted aralkyl of 7 to 15 carbons or substituted or unsubstituted aryl of 6 to 14 carbons, where the substituents for the substituted aralkyl group and the substituted aryl group for both the mono- and di-substituted carbamoyl groups are at least one of chlorine, bromine, alkyl of 1 to 8 carbons, alkenyl of 3 to 8 carbons or alkoxy of 1 to 8 carbons;

$R^8$ and $R^9$ are independently hydrogen, alkyl of 1 to 12 carbons, cycloalkyl of 5 to 12 carbons or substituted or unsubstituted aryl of 6 to 18 carbons, where the substituents are lower alkyl of 1 to 8 carbons, lower alkoxy of 1 to 8 carbons, hydroxy, bromine or chlorine; or $R^8$ and $R^9$ are linked together to form a substituted or unsubstituted alicyclic ring of 5 to 12 carbons, where the substituents are lower alkyl of 1 to 4 carbons; or $R^8$ and $R^9$ together form a substituted or unsubstituted piperidine ring of 5 to 15 carbons, where the substituents are lower alkyl of 1 to 4 carbons;

$R^{10}$ is a substituted or unsubstituted 1,2-arylene diradical of 6 to 12 carbons, a substituted or unsubstituted 1,8-naphthylene diradical of 10 to 14 carbons, a substituted or unsubstituted aralkylene diradical of 7 to 13 carbons, a substituted or unsubstituted 1,2-alkylene diradical of 2 to 10 carbons, a substituted or unsubstituted 1,3-alkylene diradical of 3 to 10 carbons, a substituted or unsubstituted alken-1,2-diyl of 2 to 10 carbons, a substituted or unsubstituted, saturated or unsaturated cycloalkylene diradical of 6 to 10 carbons or a substituted or unsubstituted, saturated or unsaturated bicycloalkylene diradical of 7 to 8 carbons, where the $R^{10}$ substituents are chlorine, bromine, alkyl of 1 to 180 carbons, alkylthio of 1 to 180 carbons, aralkylthio of 7 to 20 carbons, arylthio of 6 to 20 carbons, alkenyl of 2 to 180 carbons, aryl of 6 to 16 carbons, aralkyl of 7 to 17 carbons, carboxyl, alkoxy of 1 to 8 carbons, aryloxy of 6 to 16 carbons, alkoxycarbonyl of 2 to 10 carbons or alkoxycarbonylalkylthio of 3 to 30 carbons; and M is hydrogen or a sodium, potassium or ammonium ion.

2. The compound according to claim 1 wherein

R is hydrogen, alkyl of 1 to 14 carbons, alkenyl of 3 to 4 carbons, benzyl, 2-cyanoethyl, acetyl or benzoyl;

$R^1$ is hydrogen or methyl;

$R^2$ is an alkylene diradical of 2 to 12 carbons, an alkylene diradical of 4 to 12 carbons which contains 1 to 2 —O— or —NH— heteroatoms, with the proviso that multiple heteroatoms must be separated from each other and the diradical ends by at least one carbon atom, a cycloalkylene diradical of 5 to 12 carbons, an arylene diradical of 6 to 12 carbons or an aralkylene diradical of 8 to 12 carbons;

$R^3$ is a direct bond, an alkylene diradical of 1 to 8 carbons or an o-, m- or p-phenylene diradical;

$R^4$ is hydrogen, primary alkyl of 1 to 4 carbons, secondary alkyl of 3 to 8 carbons, benzyl or cyclohexyl;

$R^5$ is $(R^6)(R^7)N-$, $(R^8)(R^9)C=N-$, $MOC(=O)-R^{10}-C(=O)-N(R^6)-$ or

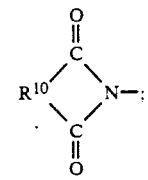

$R^6$ is hydrogen, lower alkyl of 1 to 4 carbons, cyclohexyl, benzyl or phenyl;

$R^7$ is hydrogen; methyl; ethyl; cyclohexyl; aliphatic acyl of 2 to 10 carbons; substituted or unsubstituted araliphatic acyl of 7 to 22 carbons; substituted or unsubstituted aromatic acyl of 7 to 15 carbons, where the substituents are at least one of alkyl of 1 to 5 carbons, alkoxy of 1 to 5 carbons or hydroxy, alkoxycarbonyl of 2 to 9 carbons; aryloxycarbonyl of 7 to 10 carbons; alkylcarbamoyl of 2 to 19 carbons; cycloalkylcarbamoyl of 6 to 13 carbons; arylcarbamoyl of 7 to 10 carbons or aralkylcarbamoyl of 8 to 14 carbons;

$R^8$ and $R^9$ are independently hydrogen, alkyl of 1 to 8 carbons, cycloalkyl of 5 to 6 carbons, substituted or unsubstituted aryl of 6 to 14 carbons, where the substituents are hydroxy or lower alkyl of 1 to 4 carbons, or $R^8$ and $R^9$ together form an alicyclic ring of 5 to 8 carbons or together form a tetraalkyl-substituted piperidine ring of 9 to 12 carbons;

$R^{10}$ is substituted or unsubstituted 1,2-ethanediyl, substituted or unsubstituted 1,2-propanediyl, substituted or unsubstituted 1,3-propanediyl, substituted or unsubstituted 1,2-ethenediyl, substituted or unsubstituted 1,2-cyclohexanediyl, substituted or unsubstituted cyclohex-4-ene-1,2-diyl, substituted or unsubstituted norborn-5-ene-2,3-diyl, substituted or unsubstituted 2,3-norbornanediyl, substituted or unsubstituted bicyclo[2,2,2]oct-5-ene-2,3-diyl or a substituted or unsubstituted o-phenylene diradical, where the substituents are chlorine, bromine, alkyl of 1 to 36 carbons, alkenyl of 2 to 36 carbons, aryl of 6 to 10 carbons, aralkyl of 7 to 13 carbons, alkylthio of 1 to 36 carbons, aralkylthio of 7 to 14 carbons, arylthio of 6 to 12 carbons, carboxyl, alkoxy of 1 to 8 carbons, aryloxy of 6 to 12 carbons or alkoxycarbonyl of 2 to 5 carbons; and M is hydrogen or a sodium ion.

3. The compound according to claim 2 wherein

R is hydrogen, methyl, acetyl or benzoyl;

$R^1$ is hydrogen;

$R^2$ is an alkylene diradical of 2 to 6 carbons or an oxydialkylene diradical of 4 to 8 carbons;

$R^3$ is a direct bond or an alkylene diradical of 1 to 7 carbons;

$R^4$ is hydrogen or methyl;

$R^5$ is $(R^6)(R^7)N-$, $(R^8)(R^9)C=N-$, $MOC(=O)-R^{10}-C(=O)-N(R^6)-$ or

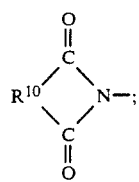

R⁶ is hydrogen;
R⁷ is hydrogen, methyl, alkylcarbamoyl of 2 to 19 carbons, phenylcarbamoyl, acetyl, propionyl, benzoyl, 3,5-di-t-butyl-4-hydroxybenzoyl, methoxycarbonyl, ethoxycarbonyl or 2-ethylhexoxycarbonyl;
$R^8$ and $R^9$ are independently lower alkyl of 1 to 4 carbons or $R^8$ and $R^9$ together form a 5 or 6-membered aliphatic ring or together form a 2,2,6,6-tetramethyl-4-piperidinyl ring;
$R^{10}$ is 1-alkylethane-1,2-diyl of 3 to 20 carbons, 1-alkenylethane-1,2-diyl of 4 to 20 carbons, 1,2-cyclohexanediyl, 4-methylcyclohexane-1,2-diyl, cyclohex-4-ene-1,2-diyl, 2,3-norbornanediyl, norborn-5-ene-2,3-diyl, an o-phenylene diradical or a 4-methoxycarbonyl-1,2-phenylene diradical; and
M is hydrogen.

4. The compound according to claim 3 wherein
R, $R^1$, $R^4$, $R^6$ and $R^7$ are hydrogen;
$R^2$ is 1,6-hexanediyl;
$R^3$ is a direct bond, a methylene diradical, 1,2-ethanediyl, 1,4-butanediyl or 1,7-heptanediyl; and
$R^5$ is $(R^6)(R^7)N-$.

5. The compound according to claim 4 where $R^3$ is a direct bond.

6. The compound according to claim 4 where $R^3$ is 1,2-ethanediyl.

7. The compound according to claim 4 where $R^3$ is 1,4-butanediyl.

8. The compound according to claim 3 wherein
R, $R^1$ and $R^4$ are hydrogen;
$R^2$ is 1,6-hexanediyl;
$R^3$ is a direct bond, a methylene diradical, 1,2-ethanediyl, 1,4-butanediyl or 1,7-heptanediyl;
$R^5$ is $(R^8)(R^9)C=N-$; and
$R^8$ and $R^9$ are independently lower alkyl of 1 to 4 carbons.

9. The compound according to claim 8 where $R^3$ is a direct bond, $R^8$ is methyl or ethyl and $R^9$ is methyl.

10. The compound according to claim 8 where $R^3$ is 1,2-ethanediyl, $R^8$ is methyl or ethyl and $R^9$ is methyl.

11. The compound according to claim 3 wherein

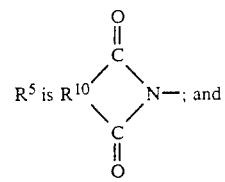

$R^{10}$ is 1,2-ethanediyl substituted by alkyl of 8 to 18 carbons or 4-methylcyclohexane-1,2-diyl.

12. The compound according to claim 11 where $R^3$ is a direct bond and $R^{10}$ is 1-(n-octyl)ethane-1,2-diyl, 1-(n-dodecyl)ethane-1,2-diyl, 1-(n-octadecyl)ethane-1,2-diyl or 4-methylcyclohexane-1,2-diyl.

13. The compound according to claim 12 where $R^{10}$ is 1-(n-dodecyl)ethane-1,2-diyl.

14. The compound according to claim 12 where $R^{10}$ is 4-methylcyclohexane-1,2-diyl.

15. The compound according to claim 11 where $R^3$ is 1,2-ethanediyl and $R^{10}$ is 4-methylcyclohexane-1,2-diyl.

16. The compound according to claim 3 wherein
$R^5$ is $MOC(=O)-R^{10}-C(=O)-N(R^6)-$;
R, $R^1$, $R^4$ and $R^6$ are hydrogen;
$R^2$ is 1,6-hexanediyl;
$R^3$ is a direct bond, a methylene diradical, 1,2-ethanediyl, 1,4-butanediyl or 1,7-heptanediyl; and
$R^{10}$ is 1-alkylethane-1,2-diyl of 10 to 20 carbons, 1-alkenylethane-1,2-diyl of 10 to 20 carbons or 4-methylcyclohexane-1,2-diyl; and
M is hydrogen.

17. The compound according to claim 16 where $R^3$ is a direct bond and $R^{10}$ is 4-methylcyclohexane-,1,2-diyl.

18. The compound according to claim 16 where $R^3$ is 1,2-ethanediyl and $R^{10}$ is 4-methylcyclohexane-1,2-diyl.

19. The compound according to claim 3 wherein
R, $R^1$, $R^4$ and $R^6$ are hydrogen;
$R^2$ is 1,6-hexanediyl;
$R^3$ is a direct bond, 1,2-ethanediyl, 1,4-butanediyl or 1,7-heptanediyl;
$R^5$ is $(R^6)(R^7)N-$; and
$R^7$ is methylcarbamoyl, butylcarbamoyl, octadecylcarbamoyl or phenylcarbamoyl.

20. The compound according to claim 19 where $R^3$ is a direct bond and $R^7$ is octadecylcarbamoyl.

21. The compound according to claim 19 where $R^3$ is 1,2-ethanediyl and $R^7$ is n-butylcarbamoyl.

22. A process for preparing the compound according to claim 4 by reacting a bis(half ester-half amide) having the formula

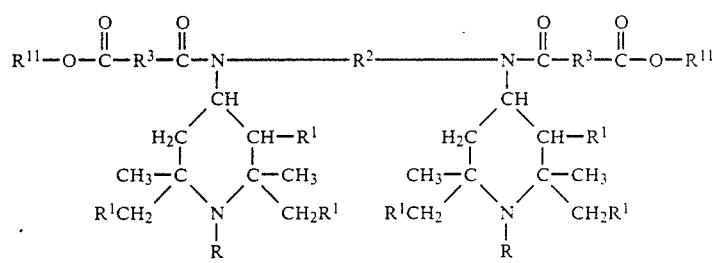

R, $R^1$ and $R^4$ are hydrogen;
$R^2$ is 1,6-hexanediyl;
$R^3$ is a direct bond, a methylene diradical, 1,2-ethanediyl, 1,4-butanediyl or 1,7-heptanediyl;

wherein $R^{11}$ is methyl or ethyl, with hydrazine or hydrazine hydrate in a molar ratio of about 2 to 1 to about 5 to 1 of the hydrazine to the bis(half ester-half amide) in methanol or ethanol and isolating the product by evaporating the alcohol, excess hydrazine and if hydrazine hydrate is used, water.

23. The process of claim 22 where $R^3$ is a direct bond and the reaction is carried out in methanol at 10° C. to 65° C. for 15 minutes to 5 hours.

24. The process of claim 22 where the reaction is carried out with refluxing in methanol for 1 hour to 4 hours and $R^3$ is 1,2-ethanediyl.

25. A process of stabilizing a synthetic or natural polymer composition subject to the degradative effects of heat or light comprising mixing with the polymer composition an amount of a compound according to claim 1 effective to stabilize the polymer composition against the degradative effects of heat or light.

26. The process of claim 25 wherein the synthetic polymer is a polyolefin, an ethylene-vinyl acetate, an acrylic polymer, a styrenic polymer, a rubber modified styrenic polymer, a polyphenylene ether, a polycarbonate, a polyamide or a mixture thereof.

27. The process of claim 26 further comprising mixing with the polymer composition about 0.01% to about 0.5% of 2,4-di-t-butylphenyl 3,5-di-t-butyl-4-hydroxybenzoate.

28. A process of stabilizing a polypropylene composition against degradative effects of heat or light comprising mixing with the composition an amount of a compound according to claim 1 effective to stabilize the composition against the degradative effects of heat or light.

29. The process of claim 28 further comprising mixing with the composition about 0.01% to about 0.5% of 2,4-di-t-butylphenyl 3,5-di-t-butyl-4-hydroxybenzoate.

30. A process for preparing the compound according to claim 2 comprising reacting a bis(half ester-half amide) having the formula

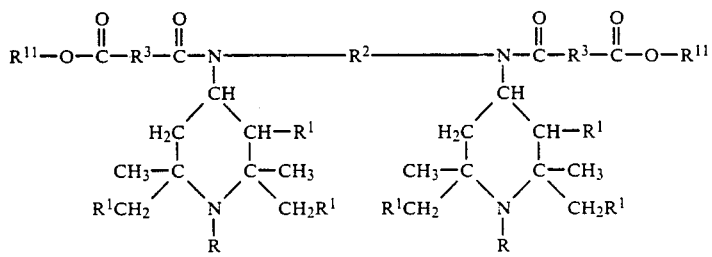

with hydrazine or hydrazine hydrate in a molar ratio of about 2 to 1 to about 5 to 1 of the hydrazine to the bis(half ester-half amide) in methanol or ethanol an isolating the product by evaporating the alcohol, excess hydrazine and of hydrazine hydrate is used, water, wherein $R^4$, $R^6$ and $R^7$ are independently hydrogen; and $R^5$ is $(R^6)(R^7)N-$; and $R^{11}$ is methyl or ethyl.

* * * * *